United States Patent
Magarvey et al.

(10) Patent No.: US 9,842,198 B2
(45) Date of Patent: Dec. 12, 2017

(54) SCREENING METHOD AND SYSTEMS UTILIZING MASS SPECTRAL FRAGMENTATION PATTERNS

(71) Applicant: McMaster University, Hamilton (CA)

(72) Inventors: Nathan Magarvey, Oakville (CA); Aubrey Bailey Morgan Wyatt, Oakville (CA); Chad William Johnston, Hamilton (CA); Ashraf Ibrahim, Etobicoke (CA); Bin Ma, Waterloo (CA); Lian Yang, Waterloo (CA)

(73) Assignee: McMaster University, Hamilton (CA)

(*) Notice: Subject to any disclaimer, the term of this patent is extended or adjusted under 35 U.S.C. 154(b) by 163 days.

(21) Appl. No.: 14/405,415

(22) PCT Filed: Jun. 5, 2013

(86) PCT No.: PCT/CA2013/050430
§ 371 (c)(1),
(2) Date: Dec. 4, 2014

(87) PCT Pub. No.: WO2013/181758
PCT Pub. Date: Dec. 12, 2013

(65) Prior Publication Data
US 2015/0148242 A1    May 28, 2015

Related U.S. Application Data

(60) Provisional application No. 61/655,752, filed on Jun. 5, 2012.

(51) Int. Cl.
| | | |
|---|---|---|
| *G01N 33/48* | (2006.01) | |
| *G01N 33/50* | (2006.01) | |
| *G06F 19/00* | (2011.01) | |
| *G01N 33/68* | (2006.01) | |
| *C40B 30/02* | (2006.01) | |
| *G06F 19/16* | (2011.01) | |
| *G06F 19/18* | (2011.01) | |
| *C40B 20/08* | (2006.01) | |
| *G01N 30/86* | (2006.01) | |
| *G01N 30/72* | (2006.01) | |

(52) U.S. Cl.
CPC ............ *G06F 19/703* (2013.01); *C40B 30/02* (2013.01); *G01N 33/6848* (2013.01); *G06F 19/16* (2013.01); *G06F 19/18* (2013.01); *C40B 20/08* (2013.01); *G01N 30/7233* (2013.01); *G01N 30/86* (2013.01)

(58) Field of Classification Search
None
See application file for complete search history.

(56) References Cited

U.S. PATENT DOCUMENTS

| | | | | |
|---|---|---|---|---|
| 2002/0012939 A1* | 1/2002 | Palsson | .............. | C12N 15/1034 |
| | | | | 435/6.13 |
| 2003/0082668 A1* | 5/2003 | Tamai | ...................... | C12Q 1/34 |
| | | | | 435/24 |
| 2005/0142584 A1 | 6/2005 | Willson et al. | | |
| 2006/0217933 A1 | 9/2006 | Wang | | |
| 2011/0171619 A1* | 7/2011 | Sweeney | ................ | G09B 23/26 |
| | | | | 434/278 |
| 2013/0116933 A1 | 5/2013 | Geromanos et al. | | |

OTHER PUBLICATIONS

Ng et al. Dereplication and de novo sequencing of nonribosomal peptides. Nature Methods, vol. 6, 2009, pp. 596-599 with online methods section and nine pages of supplemental information.*
Perkins et al. Probability-based protein identification by searching sequence databases using mass spectrometry data. Electrophoresis, vol. 20, 1999, pp. 3551-3567.*
International Search Report and Written Opinion of PCT/CA2013/050430 dated Dec. 9, 2014.
Pupin, M. et al., "Norine: A powerful resource for novel nonribosomal peptide dicovery", Synthetic and Systems Biotechnology, 1, 2016, 89-94.
Baozhen, Shan et al., "Complexities and Algorithms for Glycan Structure Sequencing using Tandem Mass Spectrometry", Proceedings, Oct. 16, 2006, 1-10.
Liu, Xiaowen et al., "Automated protein (re)sequencing with MS/MS and a homologous database yields almost full aoverage and accuracy", Bioinformatics, vol. 25, No. 17, 2009, 2174-2180.
Liu, Xiaowen et al., "Better score function for peptide identification with ETD MS/MS spectra", BMC Bioinformatics, Jan. 18, 2010, 11 (Suppl. 1):S4, 1-8.

* cited by examiner

*Primary Examiner* — Russell S Negin
(74) *Attorney, Agent, or Firm* — Bereskin & Parr LLP/S.E.N.C.R.L., s.r.l.; Patricia Folkins

(57) ABSTRACT

The present application is directed to methods and systems for identifying small molecule compounds in mixtures using a library comprising calculated structures and corresponding calculated mass spectral fragmentation patterns of known and/or hypothetical small molecule compounds that may be in the mixture and screening of a mass spectrum of the mixture using the library to identify matching fragmentation patterns. If a mass spectral fragmentation pattern present in the mass spectrum of the mixture matches a calculated fragmentation pattern of one of the known or hypothetical compounds this confirms the identity of a compound in the mixture as the known or hypothetical compound. The method represents a platform method that can be used for a multitude of purposes related to the screening and identification of compounds in mixtures. Therefore the methods and systems of the present application represent an approach that is uniquely capable of navigating chemical space and providing a understanding of desired families and pharmacophores.

30 Claims, 12 Drawing Sheets

Figure 4

A
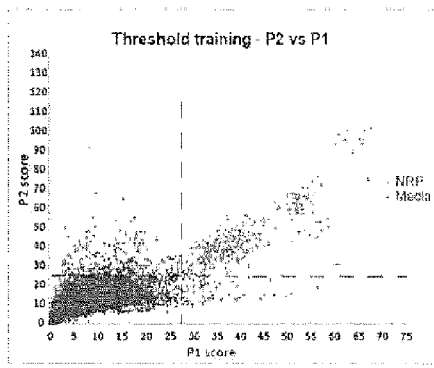

B
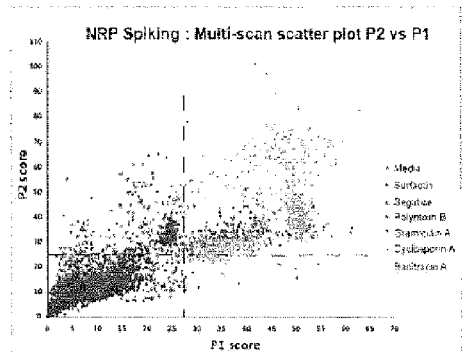

C

DDA dereplication of nonribosomal peptides in fermentation media*

| Compound | Average Rt (min) | Precursor m/z | Precursor charge | Precursor mass | Candidate mass | MS/MS Peak matches (m/z) | iSNAP - HSL (hSFs + m/z) | P1 Score** | P2 Score |
|---|---|---|---|---|---|---|---|---|---|
| Bacitracin A | 20.92 +/- 0.79 | 712.3 | 2 | 1422.6 | 1421.7 | 45 - 104 | 301 | 27.5 - 66.0 | 31.9 - 82.8 |
| Cyclosporin A | 46.66 +/- 0.86 | 602.3 | 2 | 1202.6 | 1201.84 | 134 - 163 | 329 | 61.5 - 64.4 | 32.6 - 42.3 |
| Gramicidin A | 43.53 +/- 1.15 | 942.0 | 2 | 1882.1 | 1881.07 | 73 - 117 | 375 | 32.2 - 43.6 | 30.4 - 44.4 |
| Polymyxin B | 25.03 +/- 1.94 | 402.2 | 3 | 1203.7 | 1202.75 | 46 - 58 | 249 | 27.1 - 27.9 | 36.9 - 47.3 |
| Seglitide | 23.14 +/- 0.11 | 809.8 | 1 | 808.8 | 808.43 | 44 - 47 | 96 | 45.6 - 59.2 | 29.0 - 37.4 |
| Surfactin | 50.86 +/- 0.12 | 1037.3 | 1 | 1036.3 | 1035.68 | 22 - 24 | 127 | 32.9 - 36.3 | 29.1 - 33.6 |

* iSNAP results from LC-MS/MS data in Figure 4 B
** Multiple MS/MS scans are analyzed for each compound. The scores of MS/MS spectra with the highest P1 from accross the 11 media panel is presented

Figure 12

Staphylococcus aureus Autoinducing Peptide (AIP): Ribosomal Peptide Identification

4 AIP Types

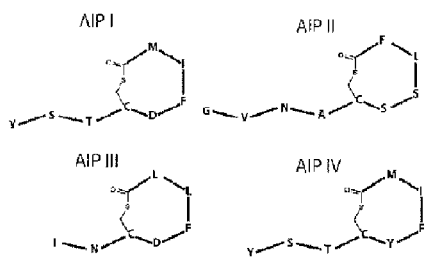

SMILES Representation

AIP I: [H]N[C@H](C(N[C@@H](CO)C(N[C@@H]([C@H](O)C)C(N[C@H](C(N[C@H](C(N[C@H](C(N[C@H](C(N1)=O)[C@@H](C)CC)=O)CC2=CC=CC=C2)=O)CC(O)=O)=O)=O)CSC([C@@H]1CCSC)=O)=O)=O)CC3=CC=C(O)C=C3

AIP II: [H]NC(N[C@@H](C(C)C)C(N[C@@H](C(N)=O)C(N[C@H](C(N[C@H](C(N[C@@H](CO)C(N[C@@H](CO)C(N[C@@H](CC(C)C)C(N1)=O)=O)=O)=O)CSC([C@@H]1CC2=CC=CC=C2)=O)=O)C)=O)=O

AIP III: O=C(C([C@@H](C)CN)NC@@H](C(N)=O)C(N[C@H](C(N[C@H](C(N[C@H](C(N[C@@H](CC(C)C)C1=O)=O)CC2=CC=CC=C2)=O)CC(O)=O)=O)CSC([C@H](CC(C)C)N1)=O)=O

AIP IV: [H]N[C@H](C(N[C@@H](CO)C(N[C@@H]([C@H](O)C)C(N[C@H](C(N[C@H](C(N[C@H](C(N1)=O)[C@@H](C)CC)=O)CC2=CC=CC=C2)=O)CC3=CC=C(O)C=C3)=O)CSC([C@@H]1CCSC)=O)=O)=O)CC4=CC=C(O)C=C4

Theoretical Fragment Hit Scoring Output

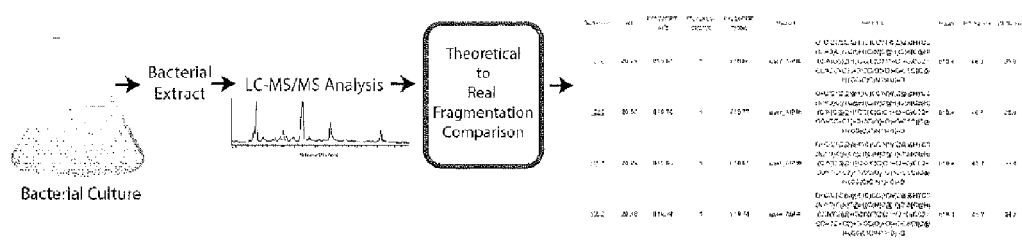

SCREENING METHOD AND SYSTEMS UTILIZING MASS SPECTRAL FRAGMENTATION PATTERNS

The present application is a National Stage of co-pending International Application No. PCT/CA2013/050430 filed on Jun. 5, 2013, which claims the benefit of priority from U.S. provisional application No. 61/655,752 filed on Jun. 5, 2012, the contents of both of which are incorporated herein by reference in their entirety.

FIELD

The present application relates to methods of screening and identifying compounds using computational chemistry in combination the mass spectrometric analysis.

BACKGROUND

Natural products serve as central pillars in human therapeutic development and are major drivers in the innovation and inspiration of drugs used in modern medicine.[1,2,3,4] Evolved chemical patterns and pharmacophores direct specific binding and lead to selective modulation of cellular processes within a clinical context.[5,6,7] Strategic exploration and expansion of privileged natural product chemical space is a key component of drug discovery, and natural products and their derivatives comprise a diverse array of clinically used antimicrobial/anticancer agents, immunomodulatory entities, and cholesterol-lowering therapies.[1,5,7] Commonly, the initial natural product hit is not optimal as a drug, and new variants must be isolated or created to realize human therapeutics with optimal efficacy, stability, and/or safety.[8,9] Methodologies from synthetic chemistry, such as diversity oriented synthesis or medicinal chemistry techniques are important contributors to drug creation from natural product leads, but they are often hindered by costly, time-consuming syntheses due to the complexity of the natural product scaffolds.[9,10] Microbes, however, are prolific in their combinatorialization around bioactive scaffolds, taking advantage of the diversity-oriented biosynthesis achieved by modular assembly lines (i.e. polyketide synthases [PKSs] and nonribosomal peptide synthetases [NRPSs]) that are chemically promiscuous, and seemingly genetically recombinogenic.[5,11,12] These natural diversity oriented biosyntheses lead to the production of series of bioactive metabolites present as dominant products or minor constituents, in concentrations that may be below the limits of bioactivity detection.[13,14,15] Sole use of bioactivity based navigation of naturally evolved drug space acts to pre-select for abundant compounds and is often confronted with isolation of knowns,[16] and is low-throughput, cumbersome, and ambiguous with respect to the chemical nature of the lead.[17,18] Microbial genomic-level information and predictions of natural products from PKS and NRPS gene clusters has exposed the wider chemical space genetically encoded molecules may occupy.[19,20,21] Accessing the full collection of natural products and explicitly these 'known unknown' molecules is suggested as a key challenge in tapping into undiscovered drug leads visible within microbial genomes.[22,23,24,25]

Longstanding fundamental challenges in natural product-based drug discovery confound integration of natural products into a perceived need for high-throughput discovery efforts.[4,7] The complexity of natural product mixtures used in screens and an inability to rapidly reveal their components are real issues that require time-consuming isolation of desired compounds from extracts in order to solve their chemical structures and avoiding known compounds. The latter issue of dereplication of knowns can be achieved in multiple ways.[18,26,27]

SUMMARY

Described herein is an approach to address longstanding small molecule natural product drug discovery issues that readily interfaces both with advanced metabolomic techniques and chemoinformatic knowledge to expand useful or underexplored chemical drug space. Herein, an informatic search program that merges chemo- and bio-informatic methodologies, leveraging thorough understanding of small molecule natural product assembly to create chemical fragmentation or "barcode" libraries has been developed to map and navigate small molecule chemical space.

Exemplary of the present methodology is the expedited identification of known compounds (dereplication) that would otherwise complicate subsequent analysis. Further, novel genetically-predicted compounds have been identified from sequenced genomes based on similarity of biosynthetic gene clusters and presumed sharing of chemical space, validating the utility of this approach for using genomic data to profile metabolomes. Partial or total structural identification of natural products have been provided in many instances, without the explicit need for isolation and further characterization. Another example is the use of expansive fragmentation, or barcode, libraries to populate hypothetical areas of chemical space occupied by a specific family of natural products to identify novel related compounds, and confirmation of this relatedness by genome sequencing. Further, the value of the present methodology for detecting desired pharmacophores has been demonstrated through the selective identification of minor structural variants bearing pre-selected site specific modifications, providing unobscured access to nature's combinatorial prowess. Within the provided examples of large libraries of fragmentation pattern chemical barcodes, the robust and accurate dereplication of knowns and detection of unknowns corresponding to their respective libraries has been demonstrated. These experiments have revealed the efficacy of this approach for detecting desired or unique agents with defined molecular patterns and pharmacophores, which serve to impart natural products with their sought after activities.

Accordingly, the present application includes a method of identifying one or more small molecule compounds from a mixture, the method comprising:

comparing a mass spectrum of the mixture with a library comprising calculated structures and corresponding calculated mass spectral fragmentation patterns of known and/or hypothetical small molecule compounds, wherein a mass spectral fragmentation pattern present in the mass spectrum of the mixture matching a calculated fragmentation pattern of one of the known or hypothetical compounds confirms the identity of a compound in the mixture as the known or hypothetical compound, and wherein the small molecule compound is a chemical compound having a molecular weight of less than or equal to about 4000 Da.

It is an embodiment that the small molecule compound is any compound any chemical compound, including polymeric substances, having a molecular weight of less than or equal to about 4000 Da and which can be analyzed by mass spectral analysis. In a further embodiment, the small molecule compound has a fragmentation pattern that is predictable and/or discernible using computational methods that generate hypothetical spectral fragments (hSFs) of chemical compounds by analyzing the structure of the chemical compound and assessing how an ionized form of the chemical compound will fragment or be generated from fragmentation induced in a mass spectrometer.

It is an embodiment that the one or more small molecule compounds are known compounds and the method is used to dereplicate the known compounds.

Rigorous testing has been done using the method of the present application and the following have been delineated as the method's features:

Dereplication was demonstrated using a nonribosomal database of hypothetical compounds and their structural fragments. These structural fragments were generated using an algorithmic analysis of SMILES linear codes. No "real" spectral library was needed for comparative analysis and positive identification/dereplication. This provides a significant cost and resources savings associated with building a natural products spectral library from "Real" data. Many of the known nonribosomal peptides are difficult to source, purify, and/or generate/obtain quality spectra.

There is no limitation to the size or structural diversity of compounds to be assessed, as compounds can readily be added to the database as a whole or through secondary databases.

Structural information can be obtained about the behavior of specific chemical structures when undergoing tandem MS (MS/MS) experiments based upon key structural fragments identified by algorithms. Specific linear or cyclic core components have unique fragmentation pathways which may become apparent through similarity screening of non-dereplicated targets through high matched scores.

Low Resolution mass spectrometry data can be used to positively identify and dereplicate small molecule compounds from complex mixtures. High Resolution Mass Accurate spectrometers are often needed for positive dereplication. Significant costs savings and increased throughput can be achieved by using Low Mass Resolution instruments in conjunction with the present methods. This makes the present method a more practical tool for identification, characterization and dereplication purposes and more applicable to a wide user base. High Resolution data can also be processed using the present methods.

The present application also includes a method of identifying one or more unknown variants of a small molecule compound in a mixture, the method comprising:

comparing a mass spectrum of the mixture with a library comprising calculated structures and corresponding calculated mass spectral fragmentation patterns of known and/or hypothetical small molecule compounds, wherein a mass spectral fragmentation pattern present in the mass spectrum of the mixture matching a calculated fragmentation pattern of one of the hypothetical variants confirms the identity of a compound in the mixture as the hypothetical variant compound and wherein the small molecule compound is a chemical compound having a molecular weight of less than or equal to about 4000 Da.

The method of the present application utilizes calculation algorithms that are amenable to computer implementation. Accordingly the present application includes a system comprising a mass spectrometer and a computer processor for performing a method of the application. In an embodiment, the system further comprises a chromatographic separator.

The computer processor is in communication with the mass spectrometer and chromatographic separator (if present).

Other features and advantages of the present application will become apparent from the following detailed description. It should be understood, however, that the detailed description and the specific examples while indicating embodiments of the application are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the drawings, in which:

FIG. 4: Shows iSNAP threshold determination and complex mixture analysis. (A) These are multiple MS/MS spectra from all six of the NRPs standards (in light grey) obtained by direct infusion experiments, overlaid with the over 6,500 MS/MS spectra from LC-MS/MS analysis of 11 microbial fermentation media, n=3, (in dark grey). The fermentation media represent the blank control in this experiment. Empirical threshold cut-offs are estimated, P1=27 and P2=24. (B) The six NRPs standards a spiked into the 11 fermentation media and subjected to LC-MS/MS analysis and iSNAP dereplication. (C) iSNAP results from the LC-MS/MS data in B, with the highest scoring MS/MS spectra from across the 11 media panel reported.

FIG. 12 shows the results of an experiment using the method of the application to identify ribosomal peptides, specifically *Staphylococcus aureus* autoinducing peptide (AIP).

DETAILED DESCRIPTION

I. Definitions

Figure 1:
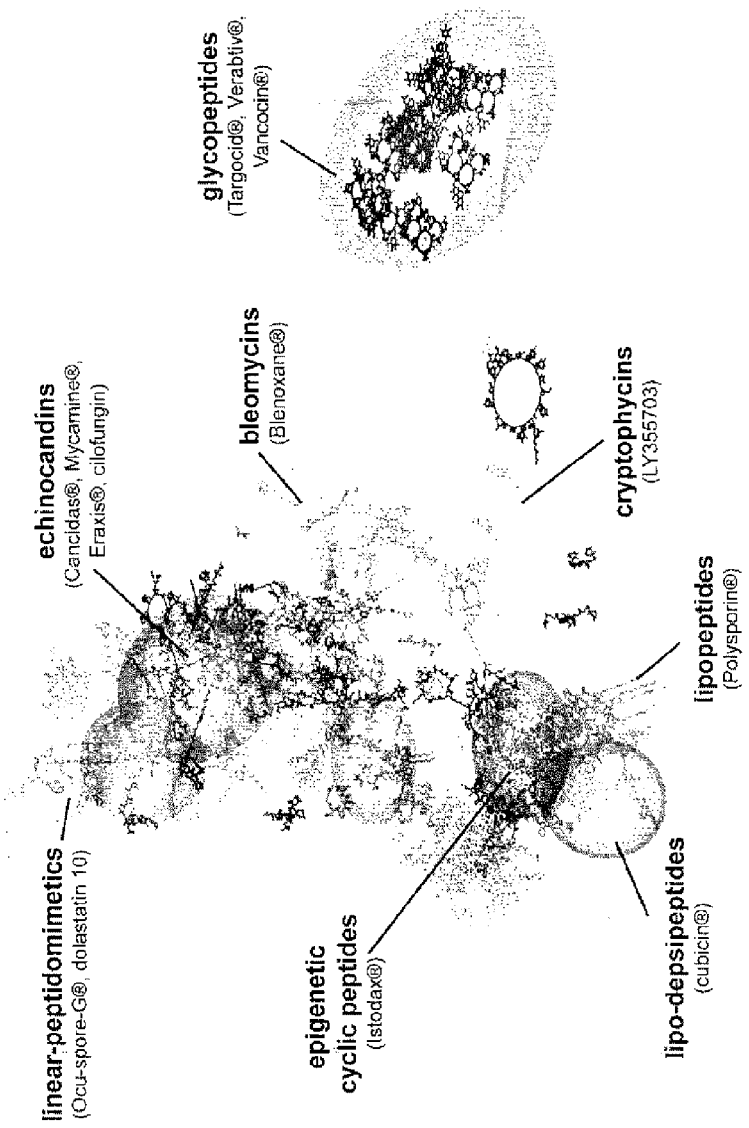
FIG. 1 shows the three-dimensional chemical space of select known nonribosomal peptide compounds. In an exemplary embodiment of the application, a series of 225 compounds taken from the iSNAP database and plotted for the following features: molecular weight, OpenBabel linear fragments (FP2), and CDK Klekota-Roth biological activity features using Chemical Space-Mapper (CheS-Mapper v1.0.27).[26] Natural product families with defined pharmacophores and activities are indicated by circles. Examples of family members that have entered clinical trials or become FDA approved drugs are indicated.[27,28,29,30,31,32]

Unless otherwise indicated, the definitions and embodiments described in this and other sections are intended to be applicable to all embodiments and aspects of the disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "Simplified Molecular Input Line Specification (SMILES)" is a linear string code that contains all the chemical information (atoms, interconnectivities and chemical architecture) of a given small molecule.[33]

The term "mass spectrum of the mixture" as used herein refers to a mass spectrum obtained using any mass spectrometric technique that corresponds to one or more compounds in a complex mixture. For example, the mass spectrum is a MS/MS obtained using tandem MS techniques and corresponds to a fragmentation pattern of one parent ion identified in the mass spectrum of the mixture.

The term "mixture" as used herein means a composition comprising at least two, and typically, a plurality of compounds having a variety of chemical compositions. In an embodiment, the mixture is a solution, or is a solid that is dissolved in a solvent to provide a solution. In an embodiment, the mixture is a complex mixture having a plurality of compounds having a variety of chemical compositions.

The term "microorganism" as used herein means an organic species selected from bacteria, viruses, fungi, archaea, protozoa, algae, microscopic plants, rotifers and planarians.

The term "library" as used herein refers to an archived collection containing many items all belonging to the same family of items. For example, a library of chemical fragmentation patterns is a collection of many different chemical fragmentation patterns, a library of natural product extracts is a collection of many different natural product extracts and a library of compounds is a collection of many different compounds. The term "many" means more than 2 or 3 and generally means as many as can be found and put into the library, therefore the size of the library is limited only upon the availability of the different components of the library. The library can also be referred to as a "database". The library can be developed by a user from data developed and stored in one or more computers, a commercially available library available through network systems, such as the Internet, or available through access through storage devices and the like.

The term "calculated mass spectral fragmentation patterns" as used herein refers to computer coded representations of hypothetical chemical fragments of a computer coded representation of a chemical compound. The fragments correspond to portions of the chemical compound that are expected, based on known fragmentation principles, to form as a result of fragmentation induced in a mass spectrometer.

The term "known" as used herein refers to a compound with a known structure and existence.

The term "unknown" as used herein refers to a compound with an unknown structure and existence.

The term "unknown known" as used herein refers to a compound whose structure is known but whose existence is unknown.

The term "hypothetical" as used herein refers to structures or fragments of structures that are predicted based on genomic homology, structural homology or calculation. Hypothetical structures or fragments are also predicted based on other substituents and structures known to exist or be available and/or based on known chemical transformations that are carried out in vivo or in vitro on compounds such as natural products.

The term "small molecule" as used herein refers to any compound that can be analyzed by mass spectral analysis having a molecular weight that is less than 4000 Da. Once a mass spectral fragmentation pattern of a compound belong to a class of compounds is determined, including new classes of compounds, a person skilled in the art would appreciate that this fragmentation pattern can be used to compute predicted and discernable fragmentation patterns for other members of that class of compounds. Accordingly, the methods of the present application are readily extendable to new (yet to be discovered) classes of compounds using the design and computational premise disclosed herein.

The term "dereplicate" or "dereplication" as used herein means a process of testing or analyzing complex mixtures so as to recognize and eliminate from consideration those active substances already studied.

The term "iSNAP" as used herein stands for informatics approach for natural products and is an acronym describing an embodiment of the method of the present application as it applies to natural products.

The term "barcode" as used herein refers to a form for representing both experimental and calculated fragmentation patterns of compounds in which ion peaks are presented as bars along a horizontal bar with spacing correlating to their actual or calculated position in a mass spectrum. Barcode representation of mass spectra are also referred to as "stick diagrams".

The term "communication", with reference to fluids, means plumbed together. The term "communication" with reference to signals, means wired, or optically linked, or radio signal linked as in wireless communication so as to receive and/or emit signals.

The term "computer processor" as used herein denotes software and firmware for use by computers, programmed computer processing units (CPUs), personal computers, servers, mainframe computers, computers and CPUs integrated with chromatographic apparatus and/or mass spectrometers or other analytical instrumentation.

The systems, processes and methods of the described embodiments of the present application are capable of being implemented in a computer program product comprising a non-transitory computer readable medium that stores computer usable instructions for one or more processors that cause the one or more processors to operate in a specific and predefined manner to perform the functions described herein. The medium may be provided in various forms, including as volatile or non-volatile memory provided on optical, magnetic or electronic storage media. That is, non-transitory computer-readable media comprise all computer-readable media, with the exception being a transitory, propagating signal. The term non-transitory is not intended to exclude computer readable media such as a volatile memory or RAM, where the data stored thereon is only temporarily stored.

II. Methods

The informatic search methods of the present application effectively detect patterns and pharmacophores of interest from within complex mixtures using MS/MS information. The present approach expedites the discovery of targeted bioactive pharmacophores and structural variations, dereplicates known compounds that would otherwise complicate subsequent analysis, and facilitates preliminary structure elucidation of novel small molecule compounds through statistically validated matching of observed and hypothetical chemical fragmentation patterns which can be represented as "barcodes".

Accordingly, the present application includes a method of identifying one or more small molecule compounds from a mixture, the method comprising:
    comparing a mass spectrum of the mixture with a library
        comprising calculated structures and corresponding
        calculated mass spectral fragmentation patterns of
        known and/or hypothetical small molecule compounds,
    wherein a mass spectral fragmentation pattern present in the mass spectrum of the mixture matching a calculated fragmentation pattern of one of the known or hypothetical compounds confirms the identity of a compound in the mixture as the known or hypothetical compound, and
    wherein the small molecule compound is a chemical compound having a molecular weight of less than or equal to about 4000 Da.

By small molecule compound, it is meant any chemical compound, including polymeric substances, having a molecular weight of less than or equal to about 4000 Da and which can be analyzed by mass spectral analysis. In an embodiment the small molecule compound has a molecular weight of less than or equal to 3500, 3000, 2500, 2000 or 1000 Da.

In an embodiment, the small molecule compound has a fragmentation pattern that is predictable and/or discernible using computational methods. Computational methods are used to generate computer codes to represent hypothetical spectral fragments (hSFs) of compounds by analyzing the chemical structure and assessing how an ionized form of the compound will fragment or be generated from fragmentation induced within a mass spectrometer. A computer program analyzes the structural code to identify the known cleavage sites in the compounds. For example, in ribosomal and nonribosomal peptides, known cleavage sites include amide bonds, therefore a computer program is created that recognizes all amide bonds in the code and generate hSFs based on amide cleavage. Fragments can arise from N-terminal (b- and a-ions) and C-terminal (y-ion) cleavage. The computer program then adds mass offsets, for example of [+H] and [+H+1] to account for protonation in positive ionization methods, and the first isotope ion, respectively. Other fragments are generated from losses of neutral species, such as water, ammonia and carbon dioxide. Computational prediction of mass fragmentation of linear ribosomal peptides is used in a number of proteomics software.[34,35,36] Cleavage sites for other chemical classes are known and include, for example, ester bonds, ether bonds and glycosidic bonds. Once a mass spectral fragmentation pattern of a compound belong to a class of compounds is determined, including new classes of compounds, a person skilled in the art would appreciate that this fragmentation pattern can be used to compute predicted and discernable fragmentation patterns for other members of that class of compounds. Accordingly, the methods of the present application are readily extendable to new (yet to be discovered) classes of compounds using the design and computational premise disclosed herein.

The calculated mass spectral fragmentation pattern for each known and/or hypothetical small molecule compound is associated with a corresponding calculated structure so that once a fragmentation pattern match is made, the small molecule compound is identified.

In an embodiment the small molecule compound is a natural product or a variant of a natural product. In a further embodiment, the natural product is produced by a microorganism. In yet another embodiment, the microorganisms are bacteria, viruses, fungi, archaea, protozoa, algae, microscopic plants, rotifers or planarians. In an embodiment, the microorganisms are bacteria.

In an embodiment, the calculated structure of the known and hypothetical compounds, and the corresponding fragmentation patterns, are entered into a library database as input SMILES codes.

In an embodiment the calculated predictable or discernible fragmentation pattern of a known or hypothetical compound is based on a modified form of a known compound.

In an embodiment, the library comprises input computer codes for structures and corresponding fragmentation patterns of analogs resulting from in vivo post-translational modifications and/or post-isolation treatment methods that cleave known groups. Post-translational modifications include, for example, glycosylations, hydroxylations, phosphoylations, sulfurations, formylations, acetylations, methylations, malonations, increases or decreases in chain length, oxidations and/or reductions. These modifications include any modification carried out in vivo using enzymes present in the organism or in a human or animal subject. Post-isolation treatments include chemical and/or enzymatic treatments that are used on samples to, for example, cleave the structure of the compounds. Such treatments, include, for example, deglycosylations, deacetylations, and/or dephosphylations.

In another embodiment, the input computer coded structures and corresponding fragmentation patterns are entered and calculated for analogs resulting from predictable alternate forms of a known compound. Such alternate forms are predictable based on known metabolic pathways, available metabolites and metabolite building blocks, genomes from other species that are known to produce similar compounds and/or genome sequencing of the species being analyzed. Some predictable alternate forms include, but are not limited to, halogenations, amidations, sulfations, alkyl group homologs, oxidized forms and/or reduced forms.

All input computer codes for structures and corresponding fragmentation patterns for known and hypothetical compounds and analogs thereof are included in the library of compounds and used for screening of complex mixtures. The greater the diversity of calculated compounds and corresponding fragmentation patterns in the library the greater chance for the identification of known or unknown known compounds in the mixture.

It is an embodiment that the one or more small molecule compounds and the known or hypothetical compounds belong to the same chemical class.

In another embodiment, the small molecule compound is selected from a nonribosomal peptide, a ribosomal peptide, a polyketide, a carbohydrate and a nucleic acid (including deoxyribonucleic acids and ribonucleic acids). In a further embodiment, the small molecule compound is selected from a nonribosomal peptide, a ribosomal peptide and a polyketide. In yet another embodiment, the small molecule compound is a nonribosomal peptide, for example as described in Schwarzer et al.[37] or Fischbach et al.[38]

In an embodiment of the application the nonribosomal peptide is selected from linear peptidomimetics, enchinocandins, bleomycins, glycopeptides, cryptophycins, lipodepsipeptides and/or epigenetic cyclic peptides as shown in FIG. 1.

In a further embodiment, the small molecule compound is any naturally occurring compound that can be characterized using mass spectral analysis and has biological activity. In an embodiment, the small molecule compound is an antibiotic, antifungal, cyctostatic, anticholesteremic, antiparasitic, coccidiostat, animal growth promoter and/or insecticide.

In an embodiment, the mixture is mixture comprising a plurality of compounds obtained from a natural source. For example, the mixture is a sample taken from any source, living or nonliving, available in nature or the environment, such as plants, animals, microorganisms, liquids, and/or soils.

In an embodiment, the mixture comprises, or is suspected of comprising, one or more biologically active compounds, or compounds that are of interest for their therapeutic potential.

In another embodiment, the mixture comprises, or is suspected of comprising, one or more natural products.

In another embodiment, the mixture comprises, or is suspected of comprising, one or more toxic or cytotoxic compounds.

In another embodiment, the mixture is an extract from a natural source, for example an extract from, or of, a microorganism, an animal or a plant. In a further embodiment, the natural source has been pre-treated, prior to extraction, to modulate, such as increase, the production of one or more small molecule compounds.

In a further embodiment, the mixture comprises or is suspected of comprising one or more metabolites from an organism, such as a microorganism. In a further embodiment, the organism has been pre-treated to modulate, such as increase, the production of one or more of its metabolites.

In an embodiment of the application, the method further comprises assessing the significance of the matching of the calculated fragmentation pattern of one of the known or hypothetical compounds with a mass spectral fragmentation pattern present in the mass spectrum of the mixture to confirm the identity of a compound in the mixture as the known or hypothetical compound. In an embodiment, the significance of the match is scored mathematically or using another suitable method.

In an embodiment, the significance of the match is scored using a combination or the raw score, the $P_1$ score and the $P_2$ score, for example, as described in the Examples below. In an embodiment, the raw score is an overall spectral match between a mass spectrum of a compound in the mixture and the calculated mass spectrum (i.e. fragmentation pattern) of a known or hypothetical compound in the library. Raw score contains a bias towards larger sized compounds containing large numbers of fragment peaks. In a further embodiment, $P_1$ and $P_2$ are probability scores that, when combined with the raw score, removes this bias. In particular, $P_1$ measures the significance of the candidate structure as compared with other structures in the database and $P_2$ is used to measure the significance of the MS spectrum compared with artificially created "decoy" spectra.

In an embodiment, the significance of the match is scored using fragment-based molecular barcodes. With barcode matching, since each bar represents an actual fragment peak in a real or calculated mass spectrum, the greater the number of bars matching between a mass spectrum of a compound in the mixture and the calculated mass spectrum (i.e. fragmentation pattern) of a known or hypothetical compound in the library, the greater the significance of the match.

In an embodiment, the mass spectrum of the mixture is obtained on any mass spectrometer employing energy fragmentation methods. The ionization mode of the spectrometer is either positive or negative. In an embodiment, the ionization mode is positive. In a further embodiment, the mass spectrum is obtained on a tandem mass spectrometer (MS/MS) instrument. In tandem mass spectrometry, precursor ions for each compound can be advantageously be identified and separately fragmented into product ions. In a further embodiment, the mass spectrum is obtained on a liquid chromatography tandem mass spectrometer (LC-MS/MS) instrument.

(i) Dereplication of Knowns

Numerous challenges are confronted in constructing natural product databases for automated dereplication of knowns. For example, for nonribosomal peptides, there is no compiled spectral database with information on all the known nonribosomal peptides or a ready supply of compounds to create one. Further there are no mathematical tools available to computationally compare unknown analytes to known nonribosomal peptides and no infrastructure existing to create hypothetical MS/MS spectra of known compounds in a rapid fashion. These issues exist for most other natural products.

As a representative example of a class of natural products, nonribosomal peptides comprise a highly privileged section of chemical space, which is diverse due to varied use of over 500 building blocks and molecular architectures (cyclic, linear, branched) and modifications and fusions with other chemical classes (i.e. polyketides). Significant to all new natural product discovery is efficient dereplication within complex extracts in a non-directed fashion. The method of the present application is the first strategy to achieve this and it has been shown to be applicable to a spectrum of nonribosomal peptide types, linear, cyclic, branched (linear and cyclic portions) and those with highly modified subunits (e.g. halogenation), mixed backbone linkages (e.g. lactones, N-methylated amides) and polyketide extensions, as well as to ribosomal peptides. False positive scores were evaluated in a number of matrices (different media compositions used for different heterotrophic bacteria) and shown to be relatively insignificant in all the media tested. Through this design a platform has been created that is robust enough to tackle a battery of differing media compositions and dereplicate the correct natural product at low nanogram levels from complex matrixes in an un-targeted fashion, using a relative low-resolution mass spectrometer. The design of the present method and its flexible use of informatic databases of natural product computer codes provides a mechanism to couple needs of dereplication with the discovery potential of novel substances revealed, for example, by microbial genomic sequencing.

Accordingly, in the method of the present application, the one or more small molecule compounds are known small molecule compounds and the method is used to dereplicate the known small molecule compounds.

The present application also includes a method of identifying one or more known small molecule compounds from a mixture, the method comprising:
comparing a mass spectrum of the mixture with a library comprising calculated structures and corresponding calculated mass spectral fragmentation patterns of known and/or hypothetical small molecule compounds,
wherein a mass spectral fragmentation pattern present in the mass spectrum of the mixture matching a calculated fragmentation pattern of one of the known compounds confirms the identity of a compound in the mixture as the known compound, and
wherein the small molecule compound is a chemical compound having a molecular weight of less than or equal to about 4000 Da.

In an embodiment, the method of the application is used to find previously known nonribosomal peptides, many of which are of significant industrial value. Some examples of such compounds include penicillin, cyclosporine, vancomycin, daptomycin, bleomycin, trichopolyn 1, efrapeptin and the like. As an example, this methodology can be used to identify these agents, and importantly analogs of these agents, which may be of significant economic value. In addition to this, the use of this approach can be implemented to identify these known compounds within natural product screening programs.

(ii) Identifying Variants of Knowns

Once the presence of a known natural product in a complex mixture is confirmed, it is useful to have a tool to determine if variants within that chemical family also exist in the mixture. The utility of the method of the present application is that new hypothetical spectral fragments derived from a hypothetical variant compound can be added to the library of calculated mass spectral fragmentation patterns (barcodes) and the method used to assess whether or not those variants are present in the mixture. This has been done in the present application with the peptaibol family of natural products and the result was the identification of 3 novel members of this family. The structures of these novel compounds was confirmed by high resolution MS and manual MS/MS annotation demonstrating that the present methodology is useful and accurate in expanding and exploring natural chemical space around known natural product structures.

Accordingly, it is an embodiment of the present application that the method is used to identify unknown variants of a known small molecule compound.

The present application also includes a method of identifying one or more unknown variants of a small molecule compound in a mixture, the method comprising:
comparing a mass spectrum of the mixture with a library comprising calculated structures and corresponding calculated mass spectral fragmentation patterns of the small molecule compound and hypothetical variants of the small molecule compound,
wherein a mass spectral fragmentation pattern present in the mass spectrum of the mixture matching a calculated fragmentation pattern of one of the hypothetical variants confirms the identity of a compound in the mixture as the hypothetical variant compound, and
wherein the small molecule compound is a chemical compound having a molecular weight of less than or equal to about 4000 Da.

(iii) Discovery of Known Unknowns Through Genome-Predicted Libraries

In the present application analysis of genomes was used to identify related biosynthetic genes encoding known natural products in organisms other than the organism known to produce the natural product. These biosynthetic gene homology searches revealed the presence of previously undescribed related genes in other organisms and complex mixtures of metabolites from these other organisms were mined using the present method to confirm and isolate these compounds. To do this, computer code for these known compounds whose presence in an organism was previously unknown (so called "unknown knowns") and their corresponding hypothetical spectral fragmentation patterns were added to the library of calculated mass spectral fragmentation patterns (barcodes).

Accordingly, it is an embodiment of the present application that the method is used to identify unknown known compounds from an organism based on genomic homology with other organisms comprising genes encoding the unknown known compounds.

Therefore the method of the present application further includes:
comparing the genome of a microorganism with the genome of a microorganism known to produce one or more known small molecule compounds;
identifying genes in the microorganism that are homologous to genes in the microorganism that produces the one or more known small molecule compounds;
if homologous genes are present in the microorganism, adding calculated structures and corresponding calculated mass spectral fragmentation patterns for the one or more known small molecule compounds to the library; and
obtaining a mass spectrum of an extract from the microorganism,
wherein a mass spectral fragmentation pattern present in the mass spectrum of the extract matching a calculated fragmentation pattern of one of the one or more known small molecule compounds confirms the identity of a compound in the extract as the known small molecule compound, and
wherein the small molecule compound is a chemical compound having a molecular weight of less than or equal to about 4000 Da.

In an embodiment, calculated structures and corresponding mass spectral fragmentation patterns for variants of the one or more known small molecule compounds are also added to the library and the method is used to identify a variant of a known small molecule compound.

(iv) Exploration of Uncharacterized Microorganism

The method of the present application is also used to screen complex mixtures from uncharacterized organisms. Therefore extracts from these uncharacterized organisms are used in the method of the application to determine if they produce small molecule compounds that exhibit structural similarities to compounds present in the library. In this way, new sources of small molecule compound families known to have biological activity are identified as well as new variants thereof.

In a representative example, an uncharacterized extract of from a natural product library was screened using the method of the present application for the presence of delftibactin-like small molecule compounds and a novel compound was identified and fully characterized using NMR spectroscopy. The structure was defined as an acylated depsipeptide with components in common with delftibactin, acidobactin and vacidobactin, including common modified ornithine units, β-hydroxy aspartic acids and serine, which indicated that this compound arose from an analogous gene cluster and was given the name variobactin A. Once the structure of this compound was known, a new library of chemical fragmentation patterns (or barcodes) was created to incorporate new sites of modification in the known scaffold, including variations in ornithine functionalization and fatty acid chain length ($C_9$-$C_{14}$). Re-testing of the original uncharacterized extract's mass spectrum in the method of the present application using the extended library revealed a series of related small molecule compounds which were named variobactin B-E. This example illustrates the utility of the method of the present application to selectively identify and locate novel small molecule compounds from selected chemical classes in complex mixtures such as libraries of natural product extracts.

(v) Identification of Site-Specific Modifications within Desired Pharmacophores

Once a microorganism is shown for the first time to produce a specific small molecule compound, for example a small molecule compound with biological activity, targeted mass spectral fragmentation patterns (or barcodes) are calculated (and corresponding calculated structures) that incorporate new predicted substitutions and modifications in the known scaffold of the small molecule compound and these patterns or barcodes are added to the library. Mixtures from the microorganism are then screened using the method of the application to determine if these hypothetical analogs of the small compound are produced by the microorganism. A representative example of this method is described in Example 2 (iv) below and illustrates how a target pharmacophore-associated chemical class can be enlarged and mapped informatically by using fragmentation pattern (barcode) libraries to identify site specific modifications of bioactive natural product leads, even when such compounds are present in vanishing quantities.

III. Systems

The method of the present application utilizes calculation algorithms that are amenable to computer implementation. Accordingly the present application includes a system comprising a mass spectrometer and a computer processor. In an embodiment, the system further comprises a chromatographic separator. The computer processor is in communication with the mass spectrometer and chromatographic separator (if present).

The computer processor will a comprise non-transitory computer readable medium. The computer readable medium will comprise a series of instructions or computer code that, when executed by the processor, will perform the method of the application. Therefore the code will cause the processor to perform one of more of the following:

(1) converting known and/or hypothetical small molecule compounds into computer readable code and calculating corresponding mass spectral fragmentation patterns of these small molecule compounds;

(2) creating a library of that comprises a calculated mass spectral fragmentation patterns for each known and/or hypothetical small molecule compound;

(3) comparing actual mass spectral fragmentation patterns of a mixture with the library comprising calculated mass spectral fragmentation patterns of known and/or hypothetical small molecule compounds; and (4) identifying mass spectral fragmentation patterns present in the mass spectrum of the mixture matching a calculated fragmentation pattern of one of the known or hypothetical compounds and confirming the identity of a compound in the mixture as the known or hypothetical compound.

The system of the present application can be implemented using a server and data storage devices configured with database(s) or file system(s), or using multiple servers or groups of servers distributed over a wide geographic area and connected via a network (e.g. Internet). Systems can reside on any networked computing device including a processor and memory, such as an electronic reading device, a personal computer, workstation, server, portable computer, mobile device, personal digital assistant, laptop, smart phone, WAP phone, an interactive television, video display terminals, gaming consoles, and portable electronic devices or a combination of these. Systems can include one or more microprocessors that can be any type of processor, such as, for example, any type of general-purpose microprocessor or microcontroller, a digital signal processing (DSP) processor, an integrated circuit, a programmable read-only memory (PROM), or any combination thereof. Systems can include any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Systems can include one or more input devices, such as a keyboard, mouse, camera, touch screen and a microphone, and can also include one or more output devices such as a display screen and a speaker. Systems can have a network interface in order to communicate with other components, to serve web pages, and perform other computing applications by connecting to any network(s) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

The present application also includes a non-transitory computer-readable medium storing one or more sequences of instructions which, when executed by one or more processors, causes the one or more processors to perform a method of the application.

The following non-limiting examples are illustrative of the present disclosure:

EXAMPLES

Example 1

Development of an Informatic Platform and Chemoinformatic Database for Natural Product Discovery of Nonribosomal Peptides Nonribosomal peptides (NRPs), represented in SMILES format, were taken from the NORINE database,[39] PubChem, the Journal of Antibiotics, and other resources. The assembled in-house NRP database for this example contained 1107 NRP structures, and for the initial part of the informatic search approach for natural products (iSNAP) a script was created that would identify all amide bonds and generate hypothetical spectral fragments (hSFs) based on amide cleavage. These hSFs are calculated estimations as to how a protonated peptide may fragment or be generated from collision-induced dissociation (CID) within the gas phase of an MS/MS experiment.[40] The iSNAP program analyzes the input SMILES codes, and identifies amide cleavage sites, enumerating every two amide combinations and cleaving at the peptide bond. The cleavage sites generate hSFs for each NRP compound. These fragments arise from the cleavage of N-terminal (b- and a-ions) and C terminal (y-ions) and the iSNAP program takes these and adds mass offsets of +H and +H+1 to account for protonation and the first isotope ion, respectively. In this way, the initial 1107 NRP structures, resulted in a hypothetical spectral library (HSL) of 100,747 hSFs. Of these 27,036 fragments resulted from amide cleavage, with each having a corresponding fragment bearing values indicative of the sequestration ionization charges (hydrogen and hydrogen plus one species) (81,108 mass-to-charge values) and neutral losses species (water, ammonia, and carbon monoxide) generating 19,639 off-set mass-to-charge values.

The collective of these hSFs comprise all of the mass-to-charge ratio ions that may be observed in real MS/MS spectra of the known NRPs. As such, a direct comparison of the hypothetical versus the experimental spectra for a given NRP should yield a significant number of shared high-intensity peaks.

Figure 2:
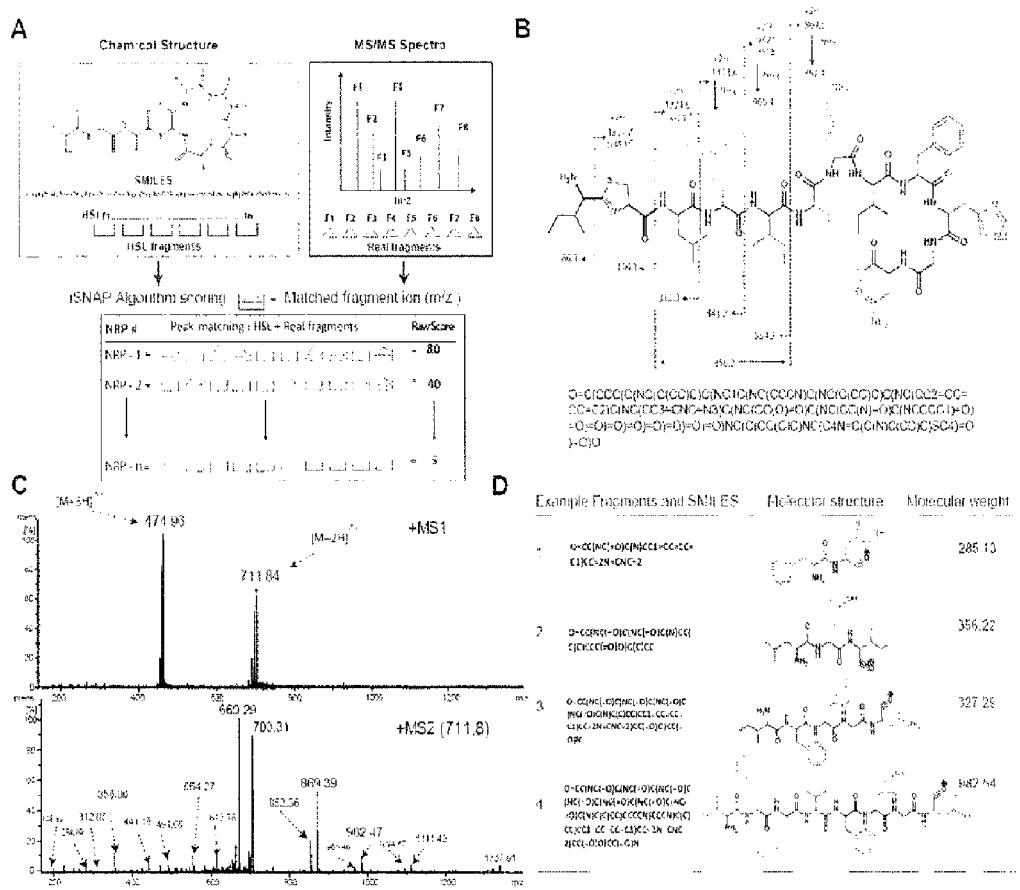
FIG. 2: shows the Chemoinformatic analysis of Bacitracin-A. (A) iSNAP Raw score calculation overview. Hypothetical spectral library fragments comprised of mass-to-charge ratios are compared with peaks from real MS/MS spectra. The matching Raw score is calculated as $\Sigma_{j=1}^{n} \log_{10}(200 \times I_j)$, where $I_1, I_2, \ldots, I_n$ are the relative intensities of the matched peaks. (B) Chemical structure, SMILES code and main fragment ions of bacitracin-A. (C) ESI-MS and MS/MS spectrum of the doubly protonated (+711.82 m/z) bacitracin-A generated by collision-induced-dissociation under automated data dependent acquisition. (D) Examples of iSNAP generated hSFs and corresponding molecular weight.

(a) Comparative Analysis of Hypothetical Mass-to-Charge Ratios and Tandem Mass Spectra for the Detection of Nonribosomal Peptides In this example, a comparison of the computational fragmentation of NRPs described above with actual NRP fragmentation was made (FIG. 2A-B). For this, the spectral fragments derived from bacitracin-A, an antimicrobial NRP comprised of both linear and cyclic portions (defined as a branched NRP) were compared with the hSFs generated by iSNAP. An authentic standard of bacitracin-A was subjected to ESI-MS/MS analysis by direct infusion with the double charged ion (+711.4 m/z) selected and subjected to CID. iSNAP analysis of bacitracin-A generated 102 hSFs and a total of 301 mass-to-charge values from these by +H and +H+1 mass offsets, in addition to neutral loss species ($H_2O$, $NH_3$, and CO). Of these, 89 mass-to-charge values could be detected by iSNAP matching algorithm from the doubly charged MS/MS spectrum (FIG. 2C-D).

(b) Creation of a Scoring Scheme (Raw Score, $P_1$ Score, and $P_2$ Score)

Having generated an NRP hypothetical spectral library (FIG. 3A), the focus became deriving a scoring mechanism to compare experimentally-generated spectra to the hypothetical spectral library. In this example, three scores were computed for these two purposes: Raw score, $P_1$ score, and $P_2$ score. Raw score is an overall spectral match between the MS/MS spectrum of an analyte and hypothetical spectrum of a known NRP. Raw score alone however, does not remove bias toward larger sized NRPs and spectra with large numbers of fragment peaks. In this way, Raw score is not a comparable measure across different spectra and therefore we derived probability scores denoted $P_1$ and $P_2$ that use raw scoring but derive match significance differently. In general, as NRPs increase in mass, the number of hSFs also increases due to the presence of potentially more amide bonds and cyclic/cyclic-branching connectivity's. With added offsets and neutral losses, the total number of hSFs can rapidly accumulate, thus the chances of falsely matching fragment ions rises, creating and artificial bias.

(i) Raw Score Calculation:

In calculating the Raw score, or spectral-matching score, iSNAP algorithm first loads the singly charged or protonated hypothetical spectrum from the database and conducts a noise filtering process to remove low intensity peaks from the input MS/MS spectra. In this process, iSNAP calculates the relative peak intensity for all the ion peaks by comparing them to the highest peak within the spectrum, and filters out peaks of less than 0.5%. This pre-filtering is applied to reduce the likelihood of randomly matched peaks, and such pre-processing is embedded within most proteomic ribosomal peptide algorithms.[34,36] The iSNAP program collects the remaining peaks and matches only those with the hypothetical spectral library. In the event that an input MS/MS spectrum is from a multiply charged ion, the algorithm adjusts the singly charged hypothetical spectrum to account for difference in charge states. The multiply charged ions are added by assuming additional protons are attached to the structural fragments. When the parent ion of the MS/MS spectrum bears a charge k, the m/z values of hypothetical fragments with charges up to k were combined to form the charge-k hypothetical spectrum. By using a mass error tolerance of 0.1 Da, the algorithm finds all spectrum peaks that have matches and computes the Raw score as $$\text{Raw score} = \sum_{\text{each matched peak } m_i} \log_{10}(200 \times \text{relative intensity of } m_i)$$

The fraction 1/0.5% (factor 200) in the formula is used to ensure a match to a peak of significant intensity (>=0.5% relatively intensity) will not contribute negatively to the overall score. Within the iSNAP algorithm a mass error tolerance of 0.1 Da is set to accommodate errors arising from use of low-resolution mass spectral files. Values set to low will limit matched fragments, and higher ones increase matches, possibly increasing random assignments.

For each MS/MS spectrum, the Raw score is calculated against the database compounds within a mass range of 0 Da to [M]+100 Da, where [M] represents parent mass. Having a relaxed mass range ensures sufficient Raw scores are calculated for statistical distribution and the upper limit of [M]+100 Da avoids a potential bias for large molecules that may score higher due to more fragment matching possibilities. The +100 Da value is chosen empirically by experimenting with +0, 50, 100, 200 and 500 Da. Only database compounds within the mass range of [M]±1 Da are considered candidate known NRPs and ultimately subjected to $P_1$ and $P_2$ calculations.

Figure 3:
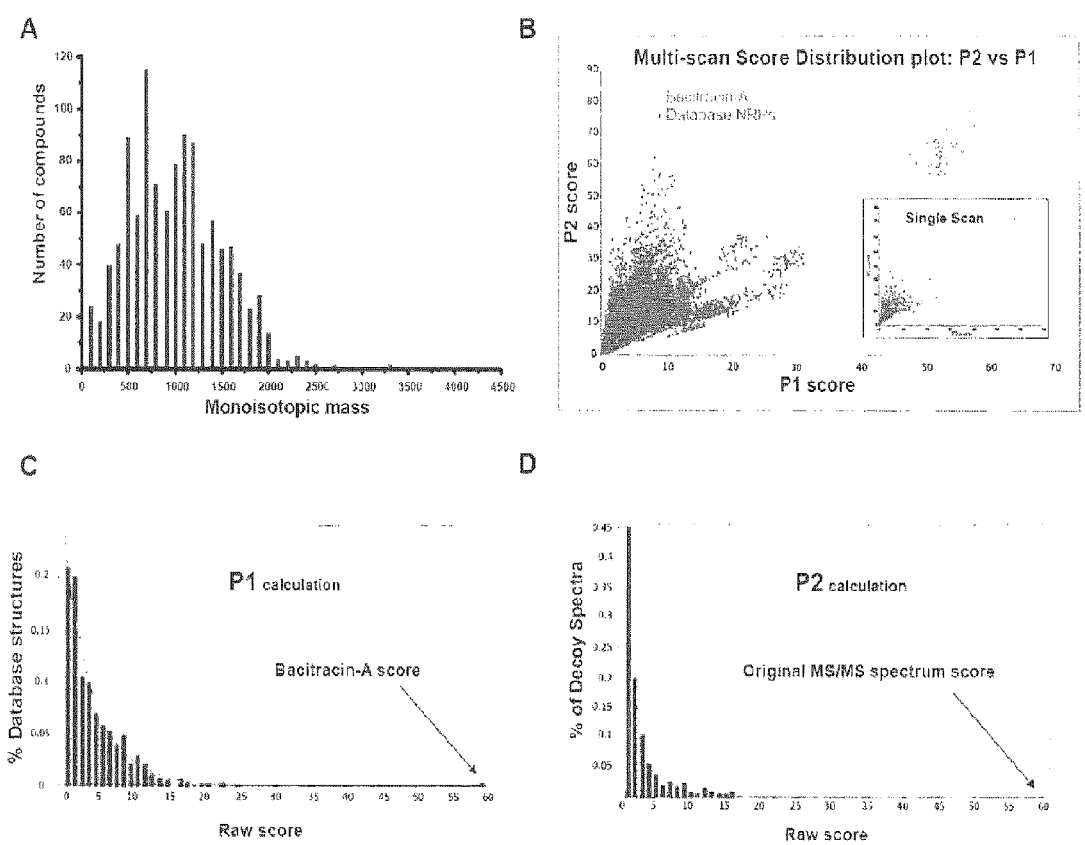
FIG. 3: Shows iSNAP scoring scheme. (A) Histogram representing the hypothetical spectral library of 1107 compounds with median of 994 Da. (B) Dereplicating bacitracin-A using the doubly protonated (+711.82 m/z) MS/MS spectra generated by subjecting a pure standard to electrospray ionization and collision-induced dissociation by direct infusion in to a Bruker Amazon-X mass spectrometer. There are multiple MS/MS scans in the data corresponding to a ~1 min infusion of bacitracin-A; each light grey point indicates a match between an MS/MS spectra and Bacitracin-A. The dark grey points show the score distribution of the other matches between the MS/MS spectra and rest of the 1106 database NRPs. The score distribution plots clearly indicate the capability of the P1 and P2 scores, in distinguishing true and false matches. (C) P1 score calculation of bacitracin-A from the doubly protonated MS/MS spectrum (+711.82 m/z). The raw score distribution is generated by scoring the MS2 spectrum against database compounds within the 0 Da to [M]+100 Da mass range. The Raw matching score of the bacitracin-A candidate is 59.1, where the p-value on the distribution is 1.74e-006. The P1 score is calculated as −10 log 10(p-value)=57.6. The fitted gamma distribution is shown as the curve. (D) P2 score calculation of bacitracin-A from the doubly protonated MS/MS spectrum (+711.82 m/z). The Raw score distribution is generated by scoring each decoy spectrum against bacitracin-A. The original spectrum has a raw score of 59.1, which is greater than that of the decoy spectra. The p-value on the distribution is 5.87e-008, with a P2 score calculated as −10 log 10(p-value)=72.31.

(ii) $P_1$ Score Calculation:

A $P_1$ score is introduced as a normalized version of the Raw score in order to add statistical significance. Empirically, when an MS/MS spectrum is scored against all database compounds within the 0 Da to [M]+100 Da mass range, the statistical distribution of the Raw scores closely fits a gamma distribution (FIG. 3C). In FIG. 3C, the fitted gamma distribution is shown as a red curve. The parameters required for a gamma distribution are estimated with the maximum-likelihood method, and the estimated gamma distribution curve is plotted to the raw scores. For each compound, the p-value is the exceedance frequency at the compound's Raw score, which is the area under the curve and to the right of the raw score. The p-value represents the probability of a random structure scoring higher with the MS/MS spectrum than the correct structure. A low p-value indicates the match is unlikely random and therefore is likely a correct one.

$$P_1 \text{ Score} = -10 \log_{10}(p\text{-value})$$

(iii) $P_2$ Score Calculation:

While the $P_1$ score measures the significance of the candidate structure as compared with other NRP structures in the database, a $P_2$ score is used to measure the significance of the MS/MS spectrum compared with artificially generated "decoy" spectra. If the MS/MS spectrum S is from an NRP structure, then the structure should be scored significantly higher using S than using the artificially generated decoy spectra. Suppose the spectrum S has a mass range from $m_1$ to $m_2$. To generate a decoy spectrum, the m/z value of each peak in S is shifted by an integer $\Delta m$. More specifically, an m/z value x is changed to $x+\Delta m$ if $x+\Delta m \leq m_2$; and to $x+\Delta m-m_2+m_1$ if $x+\Delta m>m_2$. Thus, by trying every integer $\Delta m$ between 1 and $m_2-m_1$, many decoy spectra can be obtained. The shifting method is inspired by the calculation of cross-correlation score in the SEQUEST algorithm, which was the first computer algorithm for matching ribosomal peptides in a database with MS/MS spectral data.[41] A Gamma distribution is then estimated from the Raw scores between the decoy spectra and the candidate structure. The p-value is the exceedance frequency at the original MS/MS spectrum's raw score (FIG. 3D).

$$P_2 \text{ Score} = -10 \log_{10}(p\text{-value})$$

(c) Hypothetical Spectral Library Matching Studies with Known Nonribosomal Peptides iSNAP is designed to analyze individual spectra and reveal the significance of a match between MS/MS spectra and candidate NRP compounds (those within a mass range of [M]±1 Da). For each MS/MS spectrum with established candidates, a $P_1$ score and $P_2$ score is generated for each candidate. A training experiment using six pure NRPs (bacitracin-A, cyclosporin-A, gramicidin A, polymyxin-B, surfactin, and seglitide) was used to reveal a threshold needed for true positive identification from $P_1$ and $P_2$ scores. The selection of the six NRPs was rationalized for the training experiment based on structural complexity, backbone modification (e.g. N-methylated amides, amides replaced by esters, and polyketide extended amino acid building blocks), and variance in chemical architecture (linear, cyclic, branched). The expectation from this test set was that a true candidate match will have a distinctively higher $P_1$ and $P_2$ scores.

An initial test with the branched cyclic NRP, bacitracin-A was conducted to reveal whether the designed scoring strategy would result in the true candidate having a distinctively higher $P_1$ and $P_2$ scores than those of other database structures. The resulting spectrum from an infusion experiment consisted of 56 bacitracin-A MS/MS scans and using the scoring scheme, without mass filtering ([M]±1 Da), produced bacitracin-A as the top ranking hit and was distinguishably higher than other 1106 database NRPs (see multi-scan score distribution plot of $P_2$ vs $P_1$ scores FIG. 3B).

Figure 6:
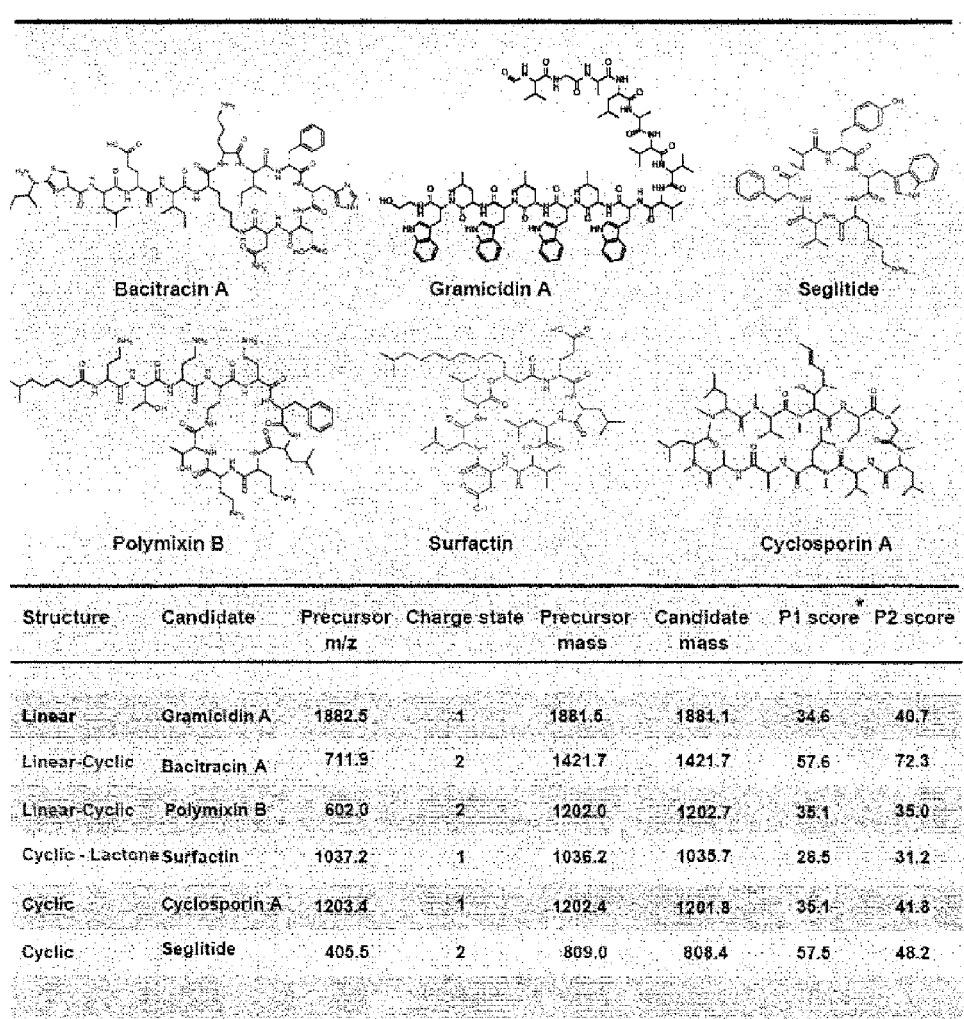
FIG. 6: shows iSNAP dereplication of linear, cyclic and cyclic-branching peptides. Chemical structures and iSNAP results of (1) bacitracin-A, (2) gramicidin, (3) seglitide, (4) polymyxin-B, (5) surfactin, (6) cyclosporin. MS/MS spectra of the six peptides were generated by subjecting a pure standard to electrospray ionization and collision-induced dissociation by direct infusion into a Bruker Amazon-X Ion trap mass spectrometer. The top score MS/MS spectra for each compound is shown. MS/MS spectra were generated under manual and automated data dependent acquisition.

Applying the scoring scheme and [M]±1 Da filter, pure standards of the five additional test compounds, cyclosporin-A, gramicidin, polymyxin-B, surfactin and seglitide, underwent manual MS/MS and automated data dependent acquisitions (DDA) (FIG. 6). In the case seglitide, a purely cyclic peptide, a doubly protonated [M+2H]$^{2+}$ species within scan #10, underwent a single stage of tandem MS and scored ($P_1$=57.5, and $P_2$=48.2) with 17 out of 30 b-ions and 27 matched mass-to-charge values. Another cyclic peptide, polymyxin-B whose complexity derives from repetitive blocks (six a,g-diaminobutyric acid residues), had the second highest number of total matched peaks at 59 with 33 b-ions matched yielding a $P_1$=35.1, and $P_2$=35.0. Matched peaks comprised of repeat amino acid units were of relative low intensity for 4 of 6 monomers. A fragmentation pattern derived from macrocyclic ring-opening, acyl chain loss and a diaminobutyric acid monomer (+963.6, +863.5 and +241 m/z) is consistent as the major pathway of fragmentation.[42] In the case of cyclosporin-A, iSNAP dereplicated the structure despite the N-methylated peptide back-bone. N-methylation limits peptide cleavage as the amide bond is unable to be protonated through intramolecular proton transfer, thus additional stability is gained by increasing the basicity of its neighboring carbonyl group, favoring a C-terminal fragmentation pathway and the generation of y-ions.[43] The highest scoring MS/MS scan came from acquisition #28, and a total of 27 hypothetical spectral library mass-to-charge values were matched to the real MS/MS spectra. Of these, 25 were b-ions, a quarter of all possible b-ion fragments and score values of $P_1$=35.1, and $P_2$=41.8. In the case of linear polypeptide gramicidin, only 5 of 85 b-ions were generated in the MS-experiment and identified (within scan #19), and overall 13 matched mass-to-charge values were sufficient for dereplication with scores above threshold cut-offs, $P_1$=34.6, and $P_2$ 40.7. In the case of another cyclic-branching peptide surfactin, 29 low intensity (<10%) peaks were matched in scan #18 of which 22 were b-ions ($P_1$=28.5, and $P_2$=31.2).

(d) Establishing iSNAP Cut-Offs for True and False Positive Rate Identification

Early stage dereplication of natural product extracts is a key goal of modern natural product screening programs and whether iSNAP enables non-targeted dereplication of known compounds in complex mixtures was probed using HPLC and low resolution tandem mass spectrometry. As microbial extracts are often comprised of complex metabolites as well as varied media constituents, it was reasoned that optimized MS/MS and LC-MS/MS settings would be required for optimal $P_1$ and $P_2$ scoring and to realize the goal of non-targeted dereplication. LC-MS/MS parameters such as mass resolution (u/sec), activation energy (q), isolation width (m/z), and data-dependent acquisition (DDA) settings were tested.

DDA acquisitions were performed under the AutoMS/MS setting with the available tuning option active, Smart parameter setting (SPS). A scan range of 100-2000 m/z was selected with precursors over 300 m/z targeted for MS/MS using the Active exclusion option set to eight spectra over a release time of 0.25 min. The Active exclusion feature enables the targeting of lower abundance ions by de-selecting and not fragmenting more abundant ions after several acquisitions have been made. A total of ten precursor ions were selected for MS/MS using the enhanced resolution mode. A baseline intensity threshold of $6\times10^5$, with an isolation width of 4 m/z was selected for the DDA experiments. $P_1$ and $P_2$ threshold cut-offs were determined through a combination of two mass spectrometry experiments. In these experiments the following queries were made: (1) Could NRPs be identified in low levels from complex matrices? (2) What false positives levels would result from the fermentation medias? and (3) Would iSNAP be capable in automatically analyzing hundreds of MS/MS spectra per a given extract? In the first experiment MS/MS spectra were generated from NRP working standards (direct infusion) and the iSNAP scores ($P_1$ and $P_2$ scores) used as positive controls in the threshold training (FIG. 4A). The second experiment, LC-MS/MS data derived from scanning of eleven common fermentation media (no NRPs added) was used to investigate false matching. As no NRP compounds exist within those matrixes, matches to NRPs within the iSNAP database must be considered as falsely matched and these low $P_1$ and $P_2$ scores are used as the negative controls. By combining the true or correct NRP database matches (NRP working standards) with the negative control false matches in a $P_2$ vs $P_1$ scatter plot, $P_1$ and $P_2$ threshold cut-offs were empirically derived (FIG. 4A). Candidates with $P_1$ and $P_2$ scores above 27 and 24, respectively are considered dereplicated or positively identified. Using the estimated thresholds, 335 of 367 MS/MS scans are identified as true candidates, with a true positive rate of 91.3%, while 24 of 6744 register as false positives, with a false positive rate of 0.0036%, from the 11 fermentation media. In an effort to further reduce false positive hits, additional filtering is applied to candidate matches with $P_1$ and $P_2$ scores above the empirical threshold. Candidates with less than 4 matched peaks were determined to contribute to false matches, while candidate matches with less than ten matched peaks, of which more than 75 percent are derived from low intensities (<2%), were also excluded.

The output of the iSNAP analysis is a complete report for each MS/MS scan; showing the scan number, retention time, precursor m/z, charge state, precursor mass and the outputted candidate's name, mass and SMILES code and number matched fragments, Raw score, $P_1$ score and $P_2$ score.

(e) Probing iSNAP Fidelity in Data-Dependent Acquisition (DDA) within Different Fermentation Conditions and Groupings of Nonribosomal Peptides Crude microbial natural product mixtures are obtained by extraction (organic solvent or resin-based) of spent fermentation broths and are thus comprised of secreted microbial small molecules and broth constituents. To reveal the suitability and fidelity of the iSNAP algorithm for screening extracts a series of liquid media varying in their spectrum of use (differing natural product producers), nutrient and peptide composition were subject to LC-MS/MS and iSNAP analysis to reveal their contributions to potential false-positives. This panel of eleven different microbial fermentation media used for fermentation of NRP producers (myxobacteria, streptomycetes and other actinobacteria, pseudomonads, bacilli and filamentous fungi) included: YPD (Yeast protein, milk protein), YMPG (yeast, malt, peptone, glucose), GYM (yeast, malt), TSB (soy protein), LB (peptone peptides and yeast protein), nutrient (beef and meat peptides from meat infusion solids), pharmamedia (cotton seed protein), grass seed veg (grass seed extract proteins), fishmeal (Fish meal protein), R2A (proteose peptone, casamino acids, yeast proteins), CY (casitone, yeast). In each of these cases the experiment was designed based on a typical volume of fermentation media used in screening (50 mL cultures) and a final amount of 50 ng of a given NRP analyzed by the mass spectrometer. A panel of NRPs were spiked into each media (yielding a final broth concentration of 50 μg/mL), and the mixture extracted with organic solvent and subjected to LC-MS/MS analysis using DDA settings (FIG. 4B). In these instances, the true and false positive rates for the study were also determined. For this, the number of MS/MS spectra acquired for each spiked media, the number of MS/MS spectra matched to the iSNAP database, MS/MS spectra from spiked-NRPs, and false matches were determined.

Automated LC-MS/MS analysis of the eleven NRP spiked fermentation media revealed as expected a variance in the numbers of product ions, with 485 being the average. In the case of R2A spiked media, a total of 192 MS/MS spectra were matched to product ion spectra and their m/z off-sets, which are derived from the six NRP candidates, of these, 126 scans were above the $P_1$ and $P_2$ cutoff. The false positive rate for R2A is calculated as the total number of MS/MS spectra (minus NRP candidates), divided by the total number of candidates with false positive hits. The false positive rate was determined to be 0.83% for R2A with only one false positive hit. The media, YMPG and Grasseed, had zero false positives detected, while the remaining media panel had between 1-4 false positive hits.

In each instance, where an NRP's product ion spectrum was generated from the spiked media extracts, iSNAP was capable of making a positive identification (FIG. 4C). However, in certain cases, some of the fermentation media had no product ions generated for two of the six standards; polymyxin-B (ie. YPD, YMPG, TSB, and Grasseed), and seglitide (ie. YPD, TSB, LB, and CY), (See Data Set 3). It was reasoned that this could be related to poor extraction efficiency, compound instability, or ion suppression in these matrices. Importantly the present studies revealed that iSNAP conducts true dereplication in a non-targeted fashion for a series of structurally diverse NRPs from various complex matrixes with an average iSNAP processing time of under a minute for each LC-MS/MS data file. The $P_1$ and $P_2$ scores of the most representative candidates for each of the six NRP spike-in compounds and media candidates are plotted in FIG. 4B with the LC-MS/MS results from the DDA analysis in FIG. 4C, highlighting the top scores across the media panels. As multiple MS/MS scans can be generated for each NRP compound, at least one scan should have an NRP candidate scored above the $P_1$ and $P_2$ thresholds for a dereplication to be made.

In the NRP spiking studies, four low scoring false positives were identified with $P_1$ and $P_2$ scores from 27-34 and 25-34 respectively. The four false positive hits have been attributed to three compounds; esperine, empedopeptin and tyrocidine C. Analysis of the detailed iSNAP report revealed that surfactin's MS/MS spectrum was incorrectly matched to that of esperine (as revealed by retention time and fragment analysis). However, the false matching of surfactin to esperine can be rationalized as they are structurally similar cyclic depsipeptides, with $C_{13}$-$C_5$ acyl chains, common monomer building blocks (L-Glu, D-Leu, and L-Asp), and esperine being within a [M]±1 Da mass range of surfactin. In comparing the $P_1$ and $P_2$ scores, esperine's were lower than that of surfactin. Analysis of surfactin's iSNAP results and matching hits has also revealed that MS/MS spectral data may be useful in revealing analogs. In the case of empedopeptin and tyrocidine C, they were matched to analytes arising from the fermentation media.

(f) Dereplicating Complex NRPs by Data-Dependent Acquisition: Kutzneride

Kutznerides are among the most complex NRPs, composed entirely of non-proteinogenic amino acids including several halogenated and oxidized groups (25-26).[44,45] In this experiment, it was tested whether or not iSNAP could dereplicate these complicated agents from extracts in a non-targeted fashion using DDA and whether novel halogenated analogs could be detected. Supernatants from *Kutzneria* sp. 744 grown in complex Merlin Norkans medium were extracted with HP20 resin and subjected to solvent partitioning, with pure organic fractions subjected to LC-MS/MS analysis. Untargeted automated analysis by iSNAP dereplicated kutzneride-1 with matched fragment peaks (+837.3, 836.3, 743.2, and 609.2 m/z). The matched fragment ions can be correlated to cleavage at the lactone ring opening (−17, −18,), and subsequent amide cleavages (−111 m/z and −245 m/z) between the 6,7-dichloro-3a-hydroxy-1,2, 3,3a, 8,-8a hexahydropyrrolo[2,3-b]indole-2-carboxylic acid and the 3-hydroxyglutamine residue (+609.2 m/z). Positive identification of kutzneride-1 was achieved using iSNAP with $P_1$ and $P_2$ scores of 31.3 and 33.4 respectively.

Frequently in modern natural product discovery simple variants of known NRP families are revealed in screening efforts. As such, it would therefore be useful to dereplicate 'probable' variants of knowns (e.g. methylated, hydroxylated or halogenated). The kutzneride producer was used to probe whether hypothetical variants of the known NRPs could be detected using the iSNAP algorithm. To promote the formation of a new kutzneride, the producing strain was grown in a medium containing bromide salts, replacing the original chloride ones. In this scenario, it was anticipated that brominated kutznerides would be biosynthesized as halogenases are known to accept either halide. As expected, the LC-MS/MS chromatogram of the resulting extract indicated the presence of the dibromo-kutzneride analog with a molecular weight of +942.1 $[M+H]^+$ and absence of kutzneride-1. Analyzing this kutzneride fraction with iSNAP did not generate hits (despite a wide candidate window of [M]+/−150 Da), and did not reveal false positives by scoring with the original kutzneride-1. Adding the dibromo-kutzneride SMILES code to the database and rerunning the previous spectra revealed that 4 high intensity fragment peaks were identified from the MS/MS spectra (+942.2, +925.2, +924.2 and +830.2 m/z), an analogous fragmentation sequence as seen for kutzneride-1, with $P_1$ and $P_2$ score values of 75.9 and 29.3 respectively. These experiments highlight the utility of the ISNAP upload feature, and how iSNAP and manipulation of known NRP SMILES codes can be used to reveal variants of known complex nonribosomal peptides.

(g) Probing the Utility of iSNAP to Interrogate Complex Extracts and Dereplicate Known Compounds Natural product screening campaigns often use bioactivity-guided fractionation to isolate active compounds. To explore how iSNAP may assist in dereplication within a bioactivity-guided fractionation campaign, it was applied to a screening of natural products for anti-staphylococcal agents. One of the natural product extracts derived from an environmental unidentified *bacillus* produced a large zone of inhibition using agar disk diffusion assays. The extract was subjected to LC-MS/MS and coordinate time-dependent fractionation into a 96 well plate. Bioactivity assays were conducted with the resulting 96 well plate with a bioluminescent *Staphylococcus aureus* strain Xen29, and the LC/MS file uploaded onto iSNAP (FIG. 5A).

Figure 5:
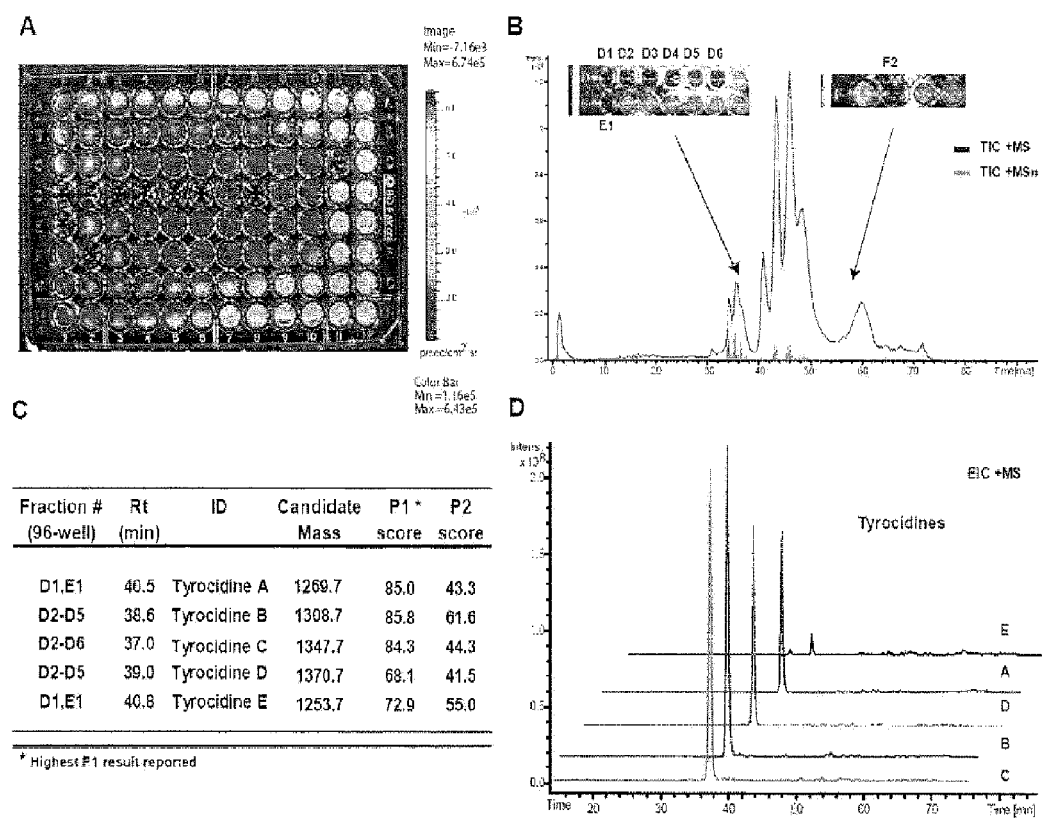
FIG. 5: Shows dereplicating bioactives from *Bacillus* sp. (A) IVIS bioluminescence imaging of crude fermentation extracts of *Bacillus* sp. revealed several bioactive regions against *Staph. aureus* (Xen29 strain), following HPLC fractionation. (B) LC-MS/MS chromatogram of *Bacillus* sp. crude extracts. Total ion chromatograms (TIC) for MS and MS(n) shown, with bioactive wells highlighted. (C) iSNAP dereplication results for *Bacillus* sp. identifying a series cyclic peptides. Tyrocidines A, B, C, D, E were dereplicated from their inputted LC-MS/MS data file in mzXML format. (D) Extracted ion chromatogram (EIC) of the dereplicated Tyrocidines from the LC-MS/MS analysis of crude extracts.

In the analysis of a crude pellet extract, a total of 1964 MS/MS scan were acquired over a 75 min LC-MS/MS run, and of these, 45 had $P_1$ and $P_2$ scores above the threshold cut off and 41 were for members of the tyrocidine family.[46] Collectively these 41 tyrocidine matches correlated with wells D1-6, D8, E1, which all lacked *S. aureus* growth. iSNAP scoring revealed high $P_1$ and $P_2$ scores for tyrocidine A ($P_1$=85, $P_2$=43.3), B ($P_1$=85.8, $P_2$=61.6), C ($P_1$=84.3, $P_2$=44.3), D ($P_1$=68.1, $P_2$=41.5), and E ($P_1$=72.9, $P_2$=55.0), from their double protonated precursor masses of +636.2, +655.8, +675.3, +686.8, and +628.2 m/z, respectively (FIG. 5B-D). High resolution mass determination of the dereplicated candidates using LTQ-Orbitrap HRS-FTMS measurements revealed the candidates were within ~0.6-4 ppm of the tyrocidines. And further comparison of the MS-MS fragmentation pattern of authentic tyrocidines with the candidate's laddering b-ions, acylium ions, provided confirmatory evidence.[47] The positive identification of each tyrocidine analog, and distinguishing between them, with increased $P_1$ and $P_2$ scores highlights the selectivity of iSNAP and detection of low abundance analogs (i.e. tyrocidine E, relative abundance is 2%).

The remaining four MS/MS spectral matches were identified as belonging to 3 compounds; capreomycin IB ($P_1$=28, $P_2$=39.4), emerimicin III ($P_1$=28.6, $P_2$=27.9), and nepadutant ($P_1$=29.7, $P_2$=57.9) Of note, however upon further investigation, capreomycin and nepadutant had only 4 matched fragments, with only one high intensity peak contributing significantly to the scoring scheme. Given these findings, it is suggested that MS/MS spectra with low matched peaks should be further examined for positive dereplication.

Example 2

Directed Discovery of Unknown Natural Products Using Fragment-Based Molecular Barcodes (a) General Experimental Procedures 1D ($^1H$ and $^{13}C$) and 2D ($^1H-^{13}C$ HMBC, HSQC, NOESY, and COSY) NMR spectra were recorded on a Bruker AVIII 700 MHz NMR spectrometer in $D_2O$ ($D_2O$; Cambridge Isotope Laboratories). High resolution MS spectra were collected on a Thermo LTQ OrbiTrap XL mass spectrometer (ThermoFisher Scientific, USA) with an electrospray ionization source (ESI) and using CID with helium for fragmentation. LCMS data was collected using a Bruker AmazonX ion trap mass spectrometer coupled with a Dionex UltiMate 3000 HPLC system, using an Ascentis Expres C18 column (150 mm×4.6 mm, Supelco) for analytical separations, running acetonitrile with 0.1% formic acid and dd$H_2O$ with 0.1% formic acid as the mobile phase.

(b) Microbial Strains

*Acidovorax citrulli* AAC00-1 and *Variovorax paradoxus* S110 were ordered from the German Resource Centre for Biological Material (DSMZ, DSM No. 17060 and 30034) and cultured on *Acidovorax* Complex Media[48] (ACM) plates at 30° C. Environmental isolates including strain P4B were found in soil samples collected around McMaster University from June to August 2010 and maintained on casitone yeast extract (CYE) or tryptic soy broth (TSB) media. Environmental isolate Elaphocordyceps sp. RKGE-151 was isolated from brown algae collected from Prince Edward Island, Canada. Isolate *Hypocrea minutispora* RKDO-344 was isolated from Great Slave Lake, Northwest Territories, Canada. *Streptomyces* sp. used for screening were obtained from other laboratories and strain repositories including DSMZ and ATCC. *Streptomyces calvus* was obtained from DSMZ (DSM No. 40010) and was cultured on mannitol soya agar.

(c) Fermentation and Small Molecule Isolation

RKDO-344 and RKGE-151 was inoculated from a 5 day shaking culture in SMYA media (10 g/L peptone, 40 g/L maltose, 10 g/L yeast extract) at 22° C. into MMK2 media (40 g/L mannitol, 5 g/L yeast extract, 4.3 g/L murashuge and Skoog salts) and grown standing at 22° C. at a 20 degree angle. Cultures were extracted with 5% XAD7 and 5% HP20 activated resins. Extracts were subjected to LC-MS/MS analysis. The mobile phase was 2% acetonitrile until 5 min and increased nonlinearly (curve 7) to 100% acetonitrile at 25 min and was held for an additional 5 min. Trichopolyn 1 eluted at 28.81 min and efrapeptin F eluted at 25.33 min. Dissolved RKDO-344 extract in 8:2 $H_2O$:MeOH was fractionated over a C18 SEP-PAK. Elution was stepwise with:

8:2 H$_2$O:MeOH 2) 1:1 H$_2$O:MeOH 3) EtOH 4) 1:1 DCM: MeOH. Trichopolyn 1 eluted in fraction 3.

A colony from a fresh plate of *A. citrulli* AAC00-1, and *V. paradoxus* S110 was inoculated into a 2.8 L glass Fernbach flask containing 1 L of *Acidovorax* Complete Media (ACM)[48]. Environmental strain *V. paradoxus* P4b was inoculated from a fresh plate into a 2.8 L glass Fernbach flask containing 1 L water, 10 g casitone, 1 g MgSO$_4$×7 H$_2$O, 1 g CaCl$_2$×2 H$_2$O, 50 mM Napes buffer, and 20 g/L HP20 resin (Dialon) with pH adjusted to 7.051. All cultures were grown at 30° C., shaking at 190 rpm for three days, after which *A. citrulli* AAC00-1 and *V. paradoxus* S110 cells were pelleted by centrifugation at 7000 rpm for 15 min. HP20 resin (Dialon) was added to the *A. citrulli* AAC00-1 and *V. paradoxus* S110 supernatant at 20 g/L and shaken for ~2 h at 220 rpm. The resin for all was harvested by Buchner funnel filtration and washed with 400 mL of distilled water. The resin was eluted three times with 400 mL of methanol. The methanol eluent was evaporated to dryness under rotary vacuum. Acidobactin A, B, C, and D were purified using a Luna 5 µm C18 column (250×10.0 mm, Phenomenex). The mobile phase was 2% acetonitrile with 0.1% formic acid, and 98% water with 0.1% formic acid at 2 minutes, increasing along curve 7 to 9% acetonitrile at 23 min at a flow rate of 6 mL/min. Acidobactin A eluted at 15.5 min, acidobactin B eluted at 15.9 min, vacidobactin A eluted at 15.7 min, and vacidobactin B eluted at 16.2 min. Variobactin was purified using a Luna 5 µm C18 column (250×15.0 mm, Phenomenex). The mobile phase was 5% acetonitrile with 0.1% formic acid, and 95% water with 0.1% formic acid at 0 min with a flow rate of 2.5 mL/min increasing to 8 mL/min at 1.5 min for an additional 3.5 min. The gradient increased linear from 5 to 10 min to 10% acetonitrile then from 10-52 min the gradient was linear to 50% acetonitrile. Variobactin A eluted at 38.03 min.

Single colonies of *S. calvus* were used to initiate 50 mL cultures of TSB, and grown for several days at 28° C. and 200 rpm. For production of WS-9326A, 10 mL of starter culture was inoculated into 1 L of production media (10 g potato dextrin, 10 g peptone, 2 g NaCl, 2 g ammonium phosphate dibasic, 1.5 g potassium phosphate monobasic, 0.5 g potassium phosphate dibasic, 0.25 MgSO$_4$×7 H$_2$O, and 5 mL of trace element solution [2 g/L MgSO$_4$, 2 g/L ZnSO$_4$×7 H$_2$O, 2 g/L FeSO$_4$×7 H$_2$O, 2 g/L MnCl$_2$×4 H$_2$O, 2 g/L CaCl$_2$×2 H$_2$O, 2 g/L NaCl, 0.4 g/L CuCl$_2$×2 H$_2$O, 0.4 g/L boric acid, 0.2 g/L sodium molybdenate hydrate, 0.2 g/L CoCl$_2$, and 2.2 g/L sodium citrate], and grown for three days at 225 rpm and 28° C. Cultures were harvested by extracting twice with 2:1 ethyl acetate and evaporating until dry. Culture extracts were resuspended in methanol and applied to an open column of LH$_2$O resin in methanol. Fractions containing WS-9326A were pooled and dried, resuspended in methanol, and analyzed by LCMS, using a Luna 5 µm C18 column (250×10.0 mm, Phenomenex) and mobile phases of acetonitrile with 0.1% formic acid, and water with 0.1% formic acid. To optimize detection of WS-9326 analogs, a method was devised with a flow rate of 1.4 mL/min, starting at 5% acetonitrile for the first 4 min, ramping with curve 7 to 42% acetonitrile by 14 min, slowly ramping with curve 7 to 53% acetonitrile by 50 min, and finally ramping with curve 7 to 100% acetonitrile by 60 min. WS-9326A eluted at 32.8 min, and the 1009 m/z analogue eluted at 28.7 min.

(d) Structure Elucidation

The structures of isolated compounds were confirmed using high resolution mass spectrometry and NMR spectrometry.

(e) Genome Sequencing

A single colony of environmental isolate P4B was grown in 3 mL TSB overnight at 30° C., 250 rpm. Genomic DNA was harvested using a GenElute Bacterial Genomic DNA Kit (Sigma). Genomic DNA was sent for library preparation and Illumina sequencing at the Farncombe Metagenomics Facility at McMaster University, using an illumine MiSeq DNA sequencer. Contigs were assembled using the ABySS genome assembly program and with Geneious bioinformatic software.

(f) Identification of Delftibactin Biosynthetic Gene Cluster and Adenylation Domain Specificity Homologous delftibactin NRPS gene clusters were found in *A. citrulli* AAC00-1, *V. paradoxus* S110 and *V. paradoxus* EPS using the BLAST function of IMG, using the delG sequence as the query. Adenylation domain specificities were assessed using NRPS Predictor or NRPS-PKS, and the 10 residue codes of each entry and its top scoring hit were recorded and compared to the delftibactin adenylation code.[49, 50, 51]

(g) MAUVE Alignment of Biosynthetic Gene Clusters

Gene cluster alignments of *D. acidovorax* SPH-1 (Daci_4756-4753), *V. paradoxus* EPS (Varpa_4327-4324), *V. paradoxus* S110 (Vapar_3746-3742), *A. citrulli* AAC00-1 (3733-3729), and environmental isolate *V. paradoxus* P4b (varC-I) were carried out in Geneious software (v5.6.4) using a progressive Mauve algorithm plugin with a seed weight of 20 and a local collinear block setting of 3000.[52]

(h) iSNAP Dereplication of Trichopolyn 1 and Efrapeptin F

Trichopolyn 1 and Efrapeptin F were identified from environmental extract 344-M3 and GE-151 respectively through the iSNAP program for dereplication as described in Example 1. As noted above, the iSNAP nonribosomal peptide SMILES database was assembled from NORINE, Pubchem, and J of Antibiotics databases, among others, and has been periodically updated to include >1100 chemical structures in SMILES code. Each of these structures are fragmented at amide bonds and neutral loss functional groups to generate a library of hypothetical structural fragments (hSFs) that are diagnostic of the real fragmented NRP. This approach was validated for a diverse array of peptide architectures, including cyclic, branched, and linear structures containing proteinogenic and nonproteinogenic amino acids.

(i) iSNAP Trichopolyn Variant Identification

A structural database of all aminoisobutyric acid (aib) and alanine combinations was created for the trichopolyn scaffolds based on trichopolyn 1 and trichopolyn B. In addition, all structural combinations of valine and isoleucine were also included to afford a final structural database consisting of 254 compounds. This combinatorial database was facilitated through the use of SmiLib v2.0 online software.[32] The 254 trichopolyn variant database was uploaded onto iSNAP and analysis was performed on the LC-MS/MS mzxmL file for the 344-M3 extract with the mass window set to one, affording only direct mass hits from the extract to the database. Structural confirmation was carried out through manual MS2 annotation, iSNAP fragment hit analysis, and high resolution mass spectroscopy.

Figure 8:
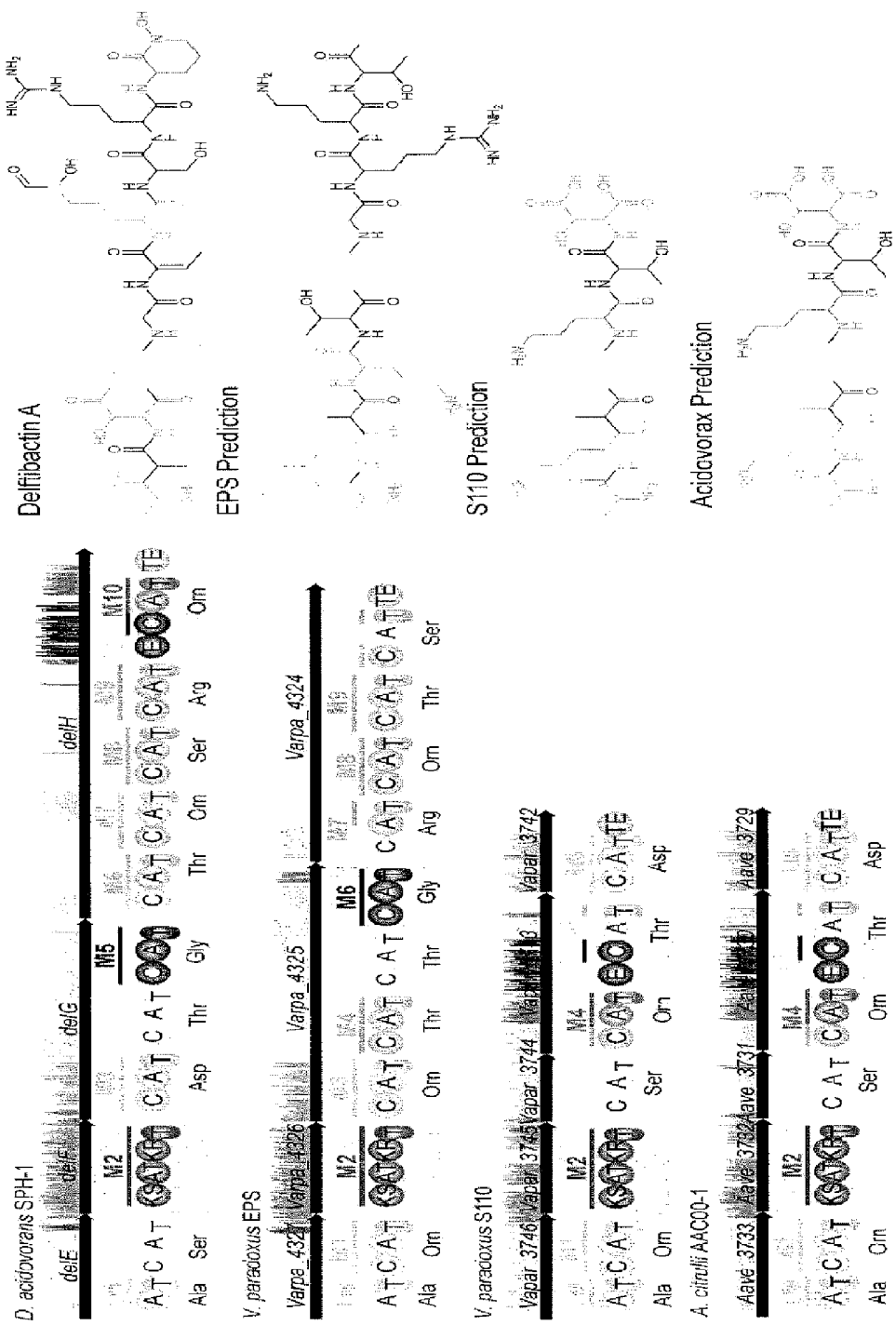
FIG. 8 shows Mauve alignment of delftibactin gene cluster and related gene clusters found in *Variovorax paradoxus* EPS (NC_014931), *V. paradoxus* S110 (NC_012791), and *Acidovorax citrulli* AAC00-1 (NC_008752). Nonribosomal peptide and polyetide genes are shown in black and the protein domain architecture is shown, where A, T, C, KS, AT, KR, E and TE are adenylation, thiolation, condensation, ketosynthase, acyltransferase, ketoreductase, epimerase and thioesterase domains respectively. Genetic similarity is indicated above the gene by mauve analysis and highlighted on the protein domains in accordance with the encoded protein domains. The amino acid specificity for each A domain is indicated as a three letter amino acid code. The structure of delftibactin A is shown and the assembly-line predicted structures for the *V. paradoxus* EPS, *V. paradoxus* S110 and *A. citrulli* AAC00-1 gene clusters are shown.

(j) iSNAP Analysis of *A. Citrulli* AAC00-1 Extract and Identification of Acidobactin A and B The acidobactin prediction database was constructed similar to above using the *A. citrulli* AAC00-1 gene cluster prediction as the scaffold (FIG. 8, 9). Variants included both cyclic and linear structures with variations of the ornithine groups (hydroxylation, formylation, and acetylation) and the polyketide portion (malonate or methyl malonate), which afforded a library of 576 compounds. The 576 compound acidobactin prediction database was uploaded onto iSNAP and analysis was performed on the LC-MS/MS mzxmL file for the *A. citrulli* AAC00-1 extract with the mass window set to fifty without P1/P2 score cutoffs. All acidobactin prediction library iSNAP scan hits were summed for each 0.25 min in retention time and plotted against retention time. These iSNAP hit frequency plots were overlaid with LC-MS/MS chromatograms for compound peak identification using Adobe Illustrator C56. Variants of acidobactin were identified using the final structure of acidobactin A as the scaffold for variant library generation, resulting in a library of 72 compounds. This identified three variant analogs,[53, 54, 55] which corresponded to acidobactin A, B and putative acidobactin C. Subsequent MS2 fragment analysis confirmed these as the true structures.

(k) iSNAP Analysis of *V. Paradoxus* S110 Extract and Identification of Vacidobactin A and B The *V. paradoxus* S110 extract was analyzed similar to *A. citrulli* AAC00-1 using the acidobactin prediction library and an iSNAP mass window of 50 without $P_1/P_2$ score cutoffs.

Figure 10:
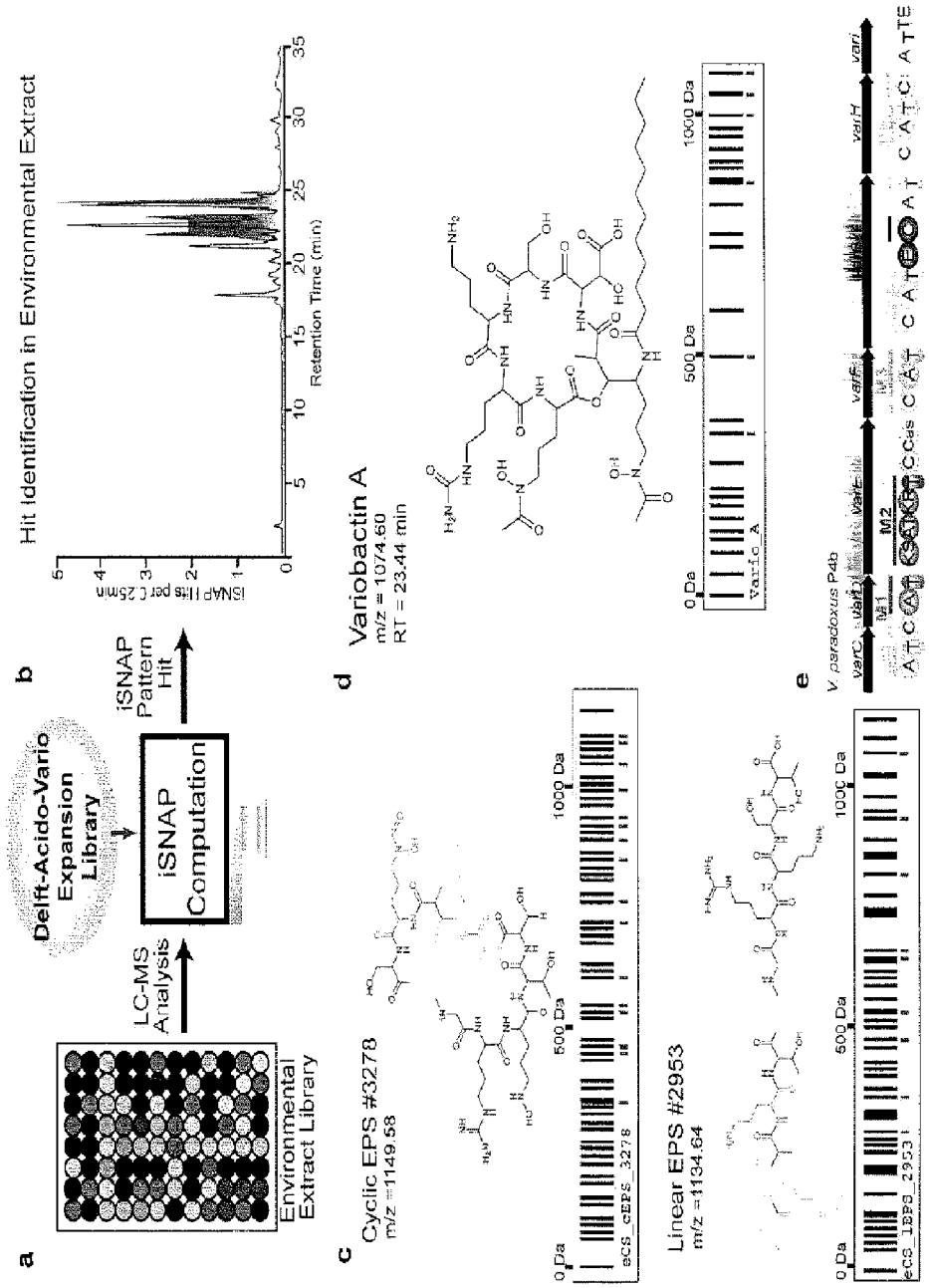
FIG. 10 shows iSNAP-guided discovery of delftibactin-acidobactin-like compound from unknown extracts. a) LC-MS screen of environmental extract library identifies prediction library iSNAP hits in unknown strain P4b. b) LC-MS base peak chromatogram of environmental strain P4b overlaid with a frequency plot of the predicted library iSNAP barcode hits per 0.25 min in LC retention time (mass window=50). c) Top iSNAP prediction library hits for environmental strain P4b showing their theoretical barcodes (black) with iSNAP detected hits (indicated by small rectangles along the bottom of the bar), predicted structure, and mass. d) Final structure of isolated iSNAP hit and novel natural product, variobactin A, including the structural barcode (black) and fragmentation hits identified by iSNAP (indicated by small rectangles along the bottom of the bar). e) Variobactin gene cluster from sequenced genome, *V. paradoxus* str. P4b. Gene similarity to related acidobactin and delftibactin gene clusters is shown using Mauve analysis (see FIG. 8).

(l) iSNAP Identification of the Delftibactin-Acidobactin-Vacidobactin-Like Compound, Variobactin A The combined prediction database was compiled using the structure of delftibactin A, the predicted structure of the *V. paradoxus* EPS, and *A. citrulli* AAC00-1 gene cluster, Variants included both cyclic and linear structures for *V. paradoxus* EPS and *A. citrulli* AAC00-1 and linear structures for delftibactin A with variations on the ornithine groups (hydroxylation, formylation, and acetylation) and the polyketide portion (malonate or methyl malonate) afforded a combined prediction library of 14,592 compounds (FIG. 10).

Extracts generated from a bacterial environmental library consisting of 80 unknown organisms were analyzed analytically by LC-MS/MS similar to the trichopolyn and efrapeptin producer extracts. Base peak ion chromatograms were converted to mzxml format using CompassXport and uploaded onto iSNAP where they were analyzed using the combined prediction database with a mass window of 50. All combined prediction library iSNAP scan hits were summed for each 0.25 min in retention time and plotted against retention time. These iSNAP hit frequency plots were overlaid with LC-MS/MS chromatograms for each environmental extract using Adobe Illustrator CS6. Strain P4b was identified from the library based on the high frequency of iSNAP hits around an unknown metabolite peak. This peak was revealed to be the novel compound, variobactin A (FIG. 10). Variobactin A variants were identified similarly to acidobactin A variants, with the exception that the final structure of variobactin A was used as the scaffold for library generation, resulting in a total of 216 variant structures.

(m) iSNAP Identification of WS-9326A and Neurokinin Alike Analogs

Figure 11:
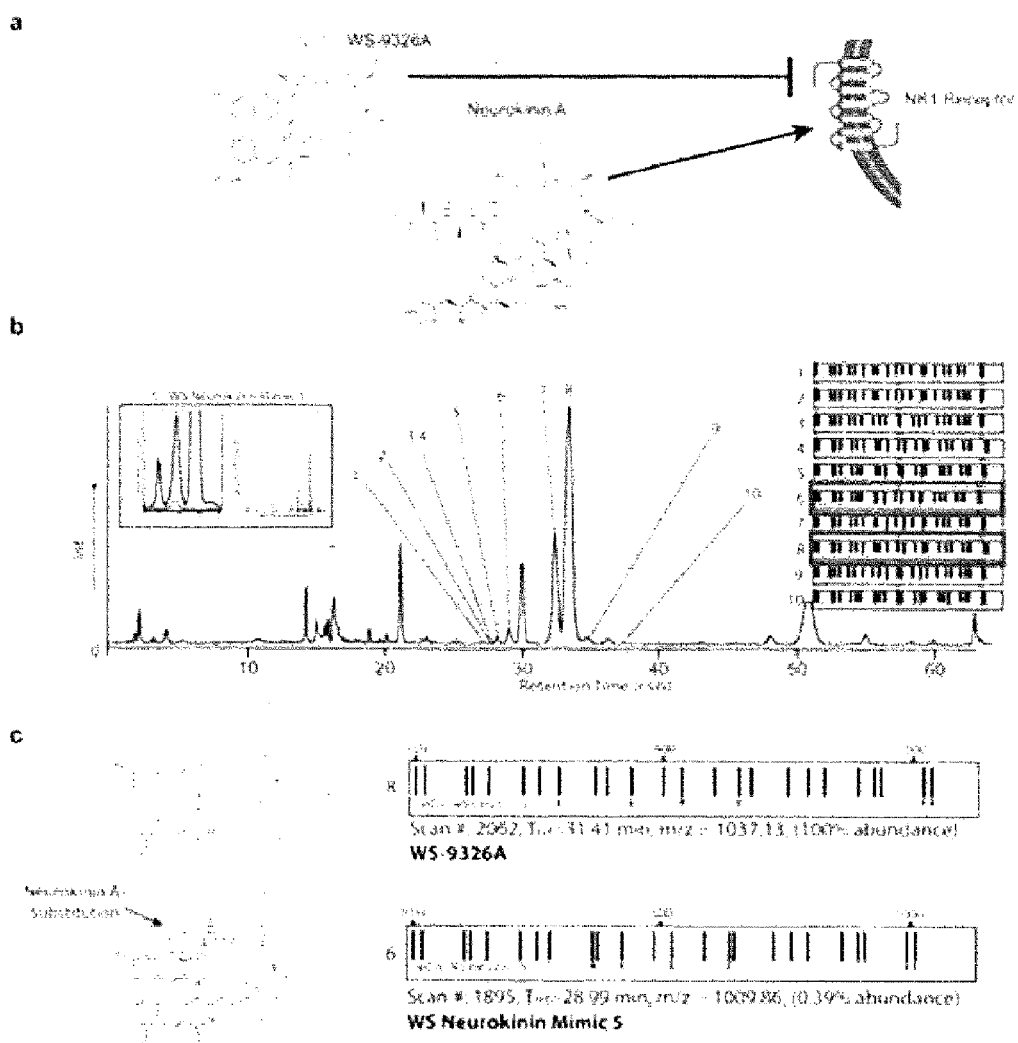
FIG. 11 shows directed discovery of Neurokinin A mimics from the iSNAP discovery of WS-9326A. a) The natural substrate (neurokinin A) and the iSNAP detected depsipeptide inhibitor (WS-9326A) for the NK-1 GPCR are shown. Structural similarities between neurokinin A and WS-9326A are labeled 1-5. b) A structural library of WS variants based on the structure of neurokinin A (WS-Neurokinin Mimic Library) was used to screen the LC-MS chromatogram using iSNAP. iSNAP detected WS-Neurokinin A mimic variants are indicated in grey on the chromatogram. The inset shows a close-up of the extracted ion chromatogram of WS Neurokinin Mimic 5 (m/z=1009) in grey. The theoretical WS-Neurokinin A mimic variant hits found within the extract are shown with their chemical barcodes (black) and iSNAP fragment hits (grey). The parent compound (WS-9326A) and the top WS-Neurokinin A mimic are highlighted. c) The iSNAP identified WS-Neurokinin A mimic library hits are shown including WSneuro_2, corresponding to WS-9326A and WSneuro_5 are shown with their structure, barcode (black) with iSNAP hits (grey), retention time and relative abundance as compared to WS-9326A. The amino acid change from leucine in the parent compound (WS-9326A) to valine (found in Neurokinin A) is highlighted on the structure of WS-Neuro_5

During the course of screening *Streptomyces* extracts, WS-9326A was identified from an extract of *S. calvus*, which was not previously known to produce the WS-9326 series of compounds. This was done using the standard iSNAP nonribosomal peptide SMILES database as outlined above. To detect analogs with increased homology to neurokinin A, a targeted library of 16 hypothetical structures was constructed to include: a serine or threonine at position 1, a valine or leucine at position 3, a serine or threonine at position 5, and a serine or threonine at position 7. This tailored 16 compound library was uploaded onto iSNAP and analysis was performed on the LC-MS/MS mzxmL file for the *S. calves* extract with the mass window set to one without P1/P2 score cutoffs. WS-9326A variants were identified and the retention time is indicated by lines overlaid on the LC-MS/MS chromatogram using Adobe Illustrator CS6 (FIG. 11).

(n) Validation of iSNAP Structural Library Specificity

The specificity of each library was verified by comparison to each extract analyzed in this study. Each iSNAP analysis indicated above was reexamined using the other iSNAP structure databases developed in this work. Comparison of the iSNAP hit frequency plots indicates mutual exclusivity of the databases for only the extracts that contain similar compounds.

Results (i) Hypothetical Barcode Libraries Identify Novel Variants of Knowns

Figure 7:
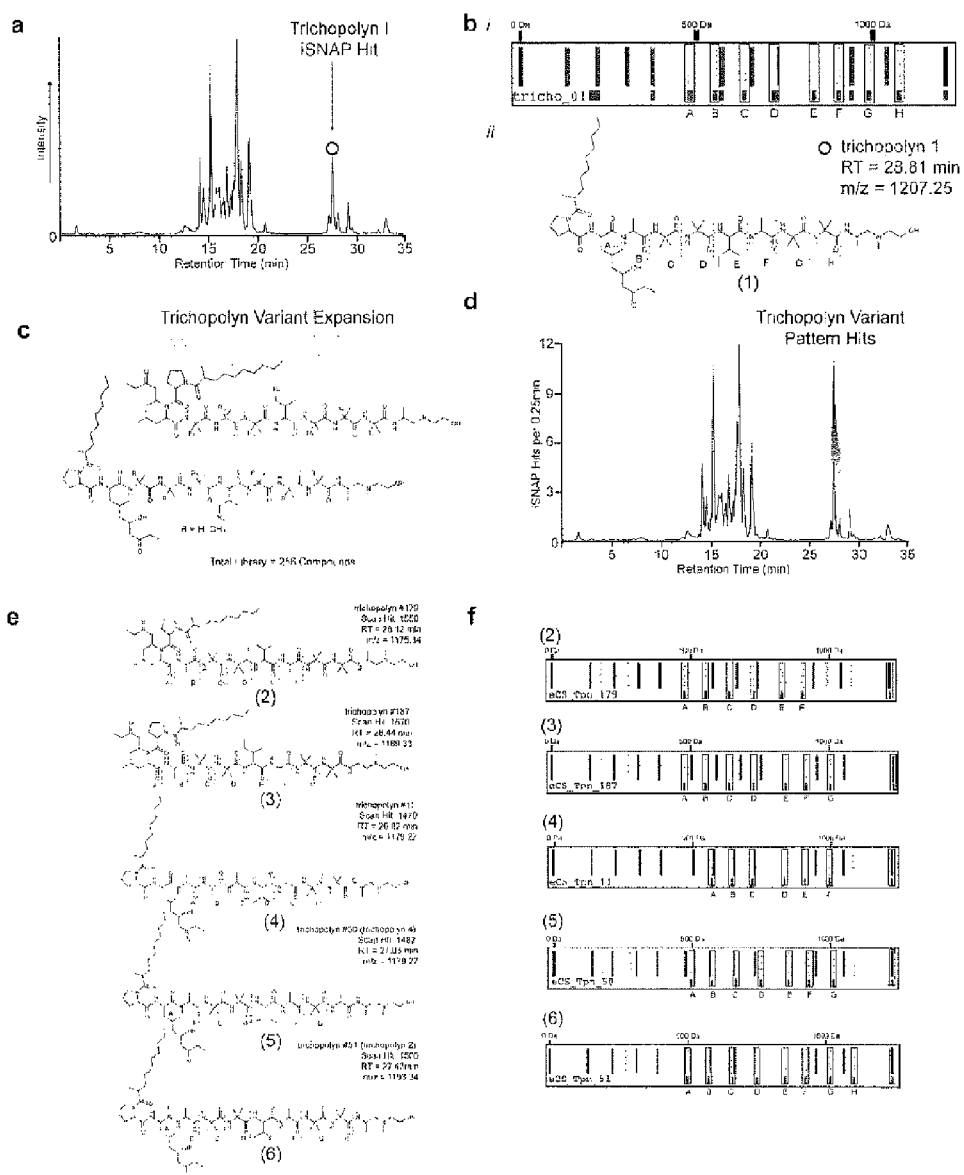
FIG. 7 shows identification of trichopolyn 1 from environmental extract bioactivity screens using informatic search for natural products (iSNAP). a) LC-MS base peak chromatogram of environmental extract, RKDO-M33, is shown with trichopolyn 1 iSNAP dereplication hit. b) Trichopolyn 1 chemical barcode and fragment matches are shown with b (light grey) and y (dark grey) ion iSNAP generated fragments and iSNAP matched fragment hits are indicated by small rectangles along the bottom of the bar (i). B-ion fragment matches are indicated below on the structure of trichopolyn 1 (ii). c) Expanded chemical space around the trichopolyn scaffold is was generated using SmiLib v2.0. d) An iSNAP direct mass hit (mass window=1 Da) frequency plot of iSNAP trichopolyn variant hits per 0.25 min in LC retention, overlaid on the 344 M3 LC-MS base peak chromatogram. e) Trichopolyn variants are identified by iSNAP. iSNAP fragment hits (indicated by small rectangles along the bottom of the bar) are indicated on the distinct iSNAP chemical barcodes of predicted b (light grey) and y (dark grey) ion fragments for each identified trichopolyn variant. B ion fragment hits are indicated on identified trichopolyn variant structures.

Within the course of a cell-based bioactivity screening campaign of a natural product extract library using the model eukaryote *Saccharomyces cerevisiae*, a number of cell death inducing extracts were identified. Microbial extracts with activity were profiled using LC-MS/MS with automated data dependent acquisition to obtain spectra and fragmentation patterns of analytes within the extract (FIG. 7a). To detect whether this bioactive extract contained known natural products, the informatic search algorithm, iSNAP (Example 1), was employed. As amino acid sequences found within peptides are specific to their identity, the MS/MS fragments of natural peptides can be used as chemical barcodes to automatically match acquired MS/MS data to barcode libraries of hypothetical MS/MS fragments, facilitating the automated identification of natural peptides within chromatograms of complex extracts without isolation followed by comprehensive structural characterization. MS/MS scans of bioactive extracts were analyzed using the iSNAP program, which identified a metabolite within the first extract at a retention time of 27.8 min whose MS/MS barcode provided a P1/P2 match score of 24/15 to that of the known peptaibol trichopolyn 1 (FIG. 7b). This structure was subsequently verified by high resolution MS and MSn fragmentation. Other extracts within this library also yielded barcode matches to known peptaibols, including efrapeptin. Peptaibols, like other natural products, have distinct chemical features (i.e. pharmacophores) that define their actions. For instance, repetitive aminoisobutryic acid (Aib) monomers frequently installed within their peptide backbones often leads to an alpha helical structure and directs membrane channel formation.[29] Interest in membrane selective peptaibols has prompted further analysis, and has led to the discovery of family members that are cancer cell specific.[30] Peptaibols are known to have a nonribosomal origin, and like other nonribosomal peptides variation occurs through tailoring modifications and nonspecific amino acid incorporation during their assembly, creating within-family diversity.[31] Currently, there are no automated strategies for unveiling variants within chemical families, or revealing their locations within extracts. The utility of a database driven approach such as iSNAP is that new barcodes can be added to the existing database for new hypothetical variants that may then be identified by iSNAP within extracts with statistical validity.

In an attempt to identify undescribed members of the peptaibol family, a barcode library of hypothetical trichopolyn variants was developed using the chemoinformatic program SmiLib v.2.0[32] to incorporate seven sites of modification within the peptide core. This approach simulated the combinations and permutations of natural product diversity that could plausibly arise from the trichopolyn assembly-line, generating 256 hypothetical variant barcodes (FIG. 7c).

These hypothetical variants were added to the defined library of NRPs currently populating iSNAP to form a new library including known and hypothetical unknown trichopolyn structures. Reanalysis of LC-MS/MS data of the trichopolyn extract with this extended barcode library enhanced the number of hits to include 3 novel and 3 known structures (FIG. 7d, e) including trichopolyn 1. The putative variants detected by iSNAP at retention times 28.81 (1), 28.12 (2), 28.44 (3), 26.82 (4), 27.03 (5), and 27.43 min (6) had MS/MS barcodes that matched the iSNAP-generated fragmentation patterns of the hypothetical variant structures #59 (1; trichopolyn 1), #179 (2), #187 (3), #11 (4), #50 (5; trichopolyn 4), and #51 (6; trichopolyn 2), corresponding to their iSNAP hits (FIG. 7e). High-resolution mass spectroscopy and manual MS/MS annotation confirmed the identity of the iSNAP variant barcode hits demonstrating that this approach is useful and accurate in expanding and exploring natural chemical space around known natural product structures (FIG. 7f). The validity of the hypothetical variant barcode approach is further illustrated by the identification of the hypothetical trichopolyn variant #59, which iSNAP correctly matched to the known structure of trichopolyn 1 from the large structure library of 256 trichopolyn variants.
(ii) Discovery of Known Unknowns Through Genome-Predicted Barcode Libraries Expanding the chemical space occupied by families of bioactive natural products is now being achieved through genomic analysis. For instance, the metagenomic interrogation of environmental samples has led to the identification of biosynthetic loci with nucleic acid sequence similarity to known natural product gene clusters.[56, 57, 58, 59] Currently, genome mining can direct efforts to select biosynthetic loci and microbes, but not to the selective detection and isolation of metabolites of interest. Correlating biosynthetic predictions, gene cluster similarities, and metabolomic data will advance genome mining efforts and facilitate the expansion of select areas of natural product chemical space. Advancing this cause will require new technologies that exploit defined molecular patterns within natural products and enable connectivity to the genes responsible for their assembly.[19, 24] Recently, a novel metallophore—delftibactin—and its' associated biosynthetic gene cluster from a microbe found on gold deposits was discovered, demonstrating that this molecule assisted in the organisms' ability to biomineralize gold.[36] The biosynthetic genes encoding the delftibactin NRPS were used to probe the GenBank database and identify related biosynthetic loci from other organisms. These biosynthetic gene homology searches revealed a series of undescribed NRPSs from organisms including *Acidovorax* (*A. citrulli* AAC00-1) and *Variovorax* (*V. paradoxus* S110 and *V. paradoxus* EPS) (FIG. 8). These uncharacterized NRPS clusters have high overall similarity and a pattern of homology that exists between the modules, indicative of common natural product architectures. Inspection of the *A. citrulli* AAC00-1 NRPS assembly-line exposed the specificity codes of the adenylation domains, which were used to generate a peptide scaffold for a barcode library of hypothetical structures (FIG. 8). Although NRPS specificity codes are known and assembly-line colinearity exists, variance frequently occurs between the core prediction and the final structure, as post assembly-line tailoring of the peptide core leads to further diversification.[13, 14, 24] While the genes responsible for these enzymatic transformations are likewise found in a given biosynthetic cluster, their sites of action are not reliably predictable. The building blocks alanine, ornithine, serine, threonine, and aspartic acid were predicted with confidence, with plausible modifications including aspartic acid β-hydroxylation, and ornithine Nδ-hydroxylation, formylation, or acetylation as determined by analysis of genes flanking the NRPS cluster. With respect to the polyketide portion of the assembly-line, variance may arise from the incorporation of either a malonate or methyl malonate. The library of hypothetical compounds was also split between linear and cyclic structures, resulting in a total of 576 hypothetical chemical barcodes.

Figure 9:
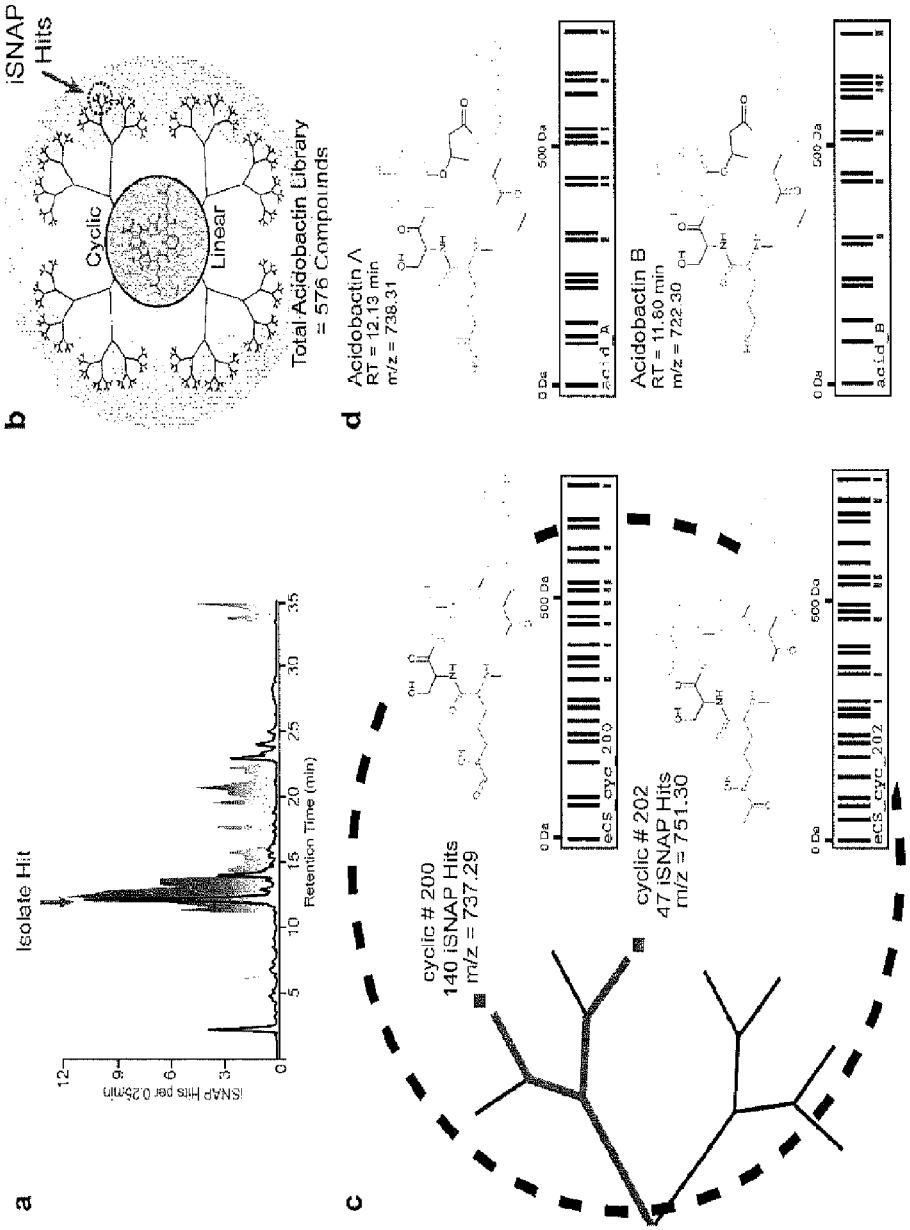
FIG. 9 shows Identification of *Acidovorax citrulli* AAC00-1 nonribosomal peptide using iSNAP with a predicted acidobactin structure database. a) *A. citrulli* AAC00-1 extract LC-MS base peak chromatogram overlaid with a frequency plot of predicted acidobactin library iSNAP barcode hits per 0.25 min in LC retention (mass window=50). b) Fractal tree representation of expanded chemical space using acidobactin prediction compound library with the two major predicted acidobactin iSNAP identified hits indicated. c) Close-up of predicted acidobactin fractal tree showing the structure of the two major iSNAP hits, their chemical barcode (black) with iSNAP fragment hits (indicated by small rectangles along the bottom of the bar), theoretical molecular weight, and retention time. d) Final structures, retention time, molecular weight, and chemical barcode fragmentation matches of the novel compounds, acidobactin A and B.

It was reasoned the iSNAP algorithm could create a means to discern the physical location and identity of the 'known unknown' natural product by utilizing the library of hypothetical chemical barcodes. To query whether this would selectively identify the predicted delftibactin-like *A. citrulli* NRP, the *A. citrulli* AAC00-1 strain was acquired, fermented, extracted with resin, and the extract interrogated for the predicted unknown. The *A. citrulli* AAC00-1 NRP barcode library was loaded into iSNAP and a precursor ion mass window of 50 Da was used to analyze the LC-MS/MS chromatogram and account for minor differences between predicted and matched structures. Taking the resulting ranking of the iSNAP hits for each scan at increasing retention time, and plotting this distribution of hits into a frequency plot over the LC chromatogram provided a ranking of the most closely matched hypothetical variants with a specific retention time (FIG. 9a). The two predominant hits are shown in a representative fractal tree which tracks sequential permutations of the chemical structures of hypothetical *A. citrulli* NRPs (FIG. 9b). These two hits occupy a common branch of this tree, indicating a high degree of similarity between the hypothetical cyclic compounds #200 (140 iSNAP hits) and #202 (47 iSNAP hits) (FIG. 9c). To probe further whether this barcode matching method for molecular pattern recognition of hypothetical compounds creates a link between genomics and metabolomics for the targeted isolation of unknown yet predicted compounds, the two compounds associated with the iSNAP hits were selectively isolated (those at retention times of 12.13 and 11.80 min). The molecules were obtained from broth extractions and their structures were determined by 1D and 2D NMR experiments, and named acidobactin A and B (FIG. 9d). Not only were these structures analogs of each other, they exhibited significant structural similarity to hypothetical compounds #200 and #202. Since the gene clusters of *A. citrulli* AAC00-1 and *V. paradoxus* S110 have extensive homology to each other, with identical adenylation domain specificity and assembly-line architecture, it was examined whether the acidobactin prediction library would succeed in identifying the unknown *Variovorax* NRP from a different metabolic background. Similar fermentation and iSNAP analysis of the *V. paradoxus* S110 extract revealed matched barcodes within the same retention time region as acidobactin A and B, with a top hit of hypothetical structure #200 (21 iSNAP hits). Subsequent isolation of iSNAP hit peaks revealed vacidobactin A and B, whose structures and MS2 fragmentation patterns were analogous to the acidobactins, with an extra methyl group derived from the PKS mediated incorporation of methyl malonate. Upon realization of the isobutyric acid substitution for the predicted alanine within the structures of acidobactin A and B (as well as the vacidobactins), a new barcoded hypothetical structure library was created, including 72 hypothetical variants of these macrocyclic compounds, incorporating more varied ornithine modifications, along with malonate and methyl malonate units. Using this refined structural library to reanalyze the original *A. citrulli* extract exposed a new hit similar to hypothetical variant #56 which eluted at 14.0 min, and upon further MS/MS analysis, is proposed to be an additional acidobactin analog, acidobactin C.

(iii) Exploration and Expansion of Targeted Areas of Chemical Space

The barcode-based targeted isolation strategy was extended to delftibactin-like molecules beyond organisms with sequenced genomes, into a natural product extract screening campaign comprising extracts from uncharacterized environmental microbes. Organisms were first profiled on the basis of whether they produced agents that exhibit likeness to a series of 14,592 hypothetical variants of delftibactin-like structures, including delftibactin, acidobactin, vacidobactin, and the predicted NRP from *V. paradoxus* EPS (FIG. 8, 10*a*). One of the extracts within the natural product library produced two significant hits including hypothetical barcodes #3278 and #2953 (FIG. 10*b, c*). The retention time of the associated hits were 23.1 min and included precursor masses of 1149.58 and 1134.64. MS-guided isolation of this peak was conducted, and subsequent scaling of broth extracts yielded sufficient quantities for structural characterization by NMR. The complete structure was assigned and defined as an acylated cyclic depsipeptide with components in common with delftibactin, acidobactin, and vacidobactin, including common modified ornithine units, β-hydroxy aspartic acids, and serine, which indicated that it may also arise from an analogous gene cluster and was given the name variobactin A (FIG. 10*d*). Following the description of this novel molecule, a new library of chemical barcodes was created to incorporate new sites of modification on the identified scaffold, including variations in ornithine decoration and fatty acid chain length (C9-C14). Re-testing the environmental extract LC-MS/MS file with this extended barcode library revealed a series of related natural products which were named variobactin B-E. The structures of these compounds were inferred from the molecular barcodes corresponding to their iSNAP hits, specifically chemical barcodes #209 (variobactin B), #210 (variobactin C), #209 (variobactin D), and #178 (variobactin E). Although variobactin B and E shared the same barcode match (#209), they differed by 2 Da and indicated a divergent unsaturation in the fatty acid tail which was not included in the variant library. This example demonstrates the utility of an informatic search strategy by selectively identifying and locating novel nonribosomal peptides from select regions of chemical space directly from natural product extracts. In total, five new cyclic lipopeptides have been defined from this isolate which appear to share a common biosynthetic origin, arising from a PKS-NRPS gene cluster that is suspected to share sequence homology with the delftibactin/acidobactin/vacidobactin gene clusters (FIG. 8). To determine if this was true, the genome of the environmental isolate P4B was sequenced and scanned for PKS-NRPS gene clusters using the acidobactin NRPS genes as a query sequence. Results from these searches revealed that it indeed harbors a PKS-NRPS assembly-line that bears significant similarity to the Delftia, *Acidovorax*, and *Variovorax* biosynthetic gene clusters (FIG. 10*e*), validating the hypothesis that hypothetical barcodes could be used to populate chemical space and identify related unknown molecules.

(iv) Identification of Site Specific Modifications within Desired Pharmacophores While screening natural product extracts for both known and predicted molecules using iSNAP, a strain of *Streptomyces calvus* was identified as a novel producer of the lipodepsipeptide WS-9326A, and was confirmed with 1D and 2D NMR experiments. Though this strain had previously been studied for production of anti-bacterial and anti-trypanosomal compounds,[37] this new molecule functions as a potent antagonist of the G-protein coupled receptor NK-1,[38, 39] whose natural ligands are tachykinin peptide hormones such as neurokinin A[40] (FIG. 11*a*). Neuropeptide mimics, accessed through synthesis or targeted isolation, have been well characterized as potent modulators of GPCR activity.[41] Analysis of the WS-9326A structure revealed that a large portion bore a significant resemblance to neurokinin A (FIG. 11*a*) which could seemingly explain its potent antagonistic activity. To identify analogs of WS-9326A with increased similarity to neurokinin A, a targeted barcode library with combinatorialized substitutions at macrocycle ring positions 1, 3, 5, and 7 was generated, where modifications may lead to increased homology. This targeted library was used with a mass window of one to exclusively identify specified analogs from a culture extract of *S. calvus*. A series of barcodes matching WS-9326A variants were identified, including recently described congeners,[42] and novel analogs with increased homology to neurokinin A through detected amino acid substitutions (FIG. 11*b*). One minor analog, which co-elutes with several other structural analogs and was produced at 0.4% the titer of WS-9326A, was shown to possess serine and valine substitutions at peptide macrocycle positions 1 and 3, and was targeted for time-dependent fractionation using the iSNAP directed retention time of 28.9 min (FIG. 11*c*). Subsequent MS/MS and NMR studies confirmed the match to the hypothetical chemical barcode. This example outlines how a target pharmacophore-associated chemical space can be enlarged and mapped informatically by using barcode libraries to identify site specific modifications of bioactive natural product leads, even when such compounds are present in vanishing quantities.

Example 3

Identifying Ribosomal Peptides Using iSNAP Algorithm

The iSNAP algorithm was used to identify autoinducing peptides (AIP) from *Staphylococcus aureus*. The results are shown in FIG. 12.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

[1] Newman, D. J. & Cragg, G. M. Natural Products As Sources of New Drugs over the 30 Years from 1981 to 2010. *J. Nat. Prod.* 75, 311-335 (2012).

[2] Carter, G. T. Natural products and Pharma 2011: strategic changes spur new opportunities. *Nat. Prod. Rep.* 28, 1783-1789 (2011).

[3] Koehn, F. E. & Carter, G. T. Rediscovering natural products as a source of new drugs. *Discov. Med.* 5, 159-164 (2005).

[4] Koehn, F. E. & Carter, G. T. The evolving role of natural products in drug discovery. *Nat. Rev. Drug Discov.* 4, 206-220 (2005).

[5] Clardy, J. & Walsh, C. Lessons from natural molecules. *Nature* 432, 829-837 (2004).

[6] Lipinski, C. & Hopkins, A. Navigating chemical space for biology and medicine. *Nature* 432, 855-861 (2004).

[7] Li, J. W. & Vederas, J. C. Drug discovery and natural products: end of an era or an endless frontier? *Science* 325, 161-165 (2009).

[8] Tobert, J. A. Lovastatin and beyond: the history of the HMG-CoA reductase inhibitors. *Nat. Rev. Drug Discov.* 2, 517-526 (2003).

[9] Gregg, G. M., & Newmann, D. J. Nature: a vital source of leads for anticancer drug development. *Phytochem. Rev.* 8, 313-331 (2009).

[10] Gregory, M. A. et al. Mutasynthesis of rapamycin analogues through the manipulation of a gene governing started unit biosynthesis. *Angew. Chem. Int. Ed.* 117, 4835-4838 (2005).

[11] Gu, L. et al. Metamorphic enzyme assembly in polyketide diversification. *Nature* 459, 731-735 (2009).

[12] Sherman, D. H. The Lego-ization of polyketide biosynthesis. *Nat. Biotechnol.* 23, 1083-1084 (2005).

[13] Starks, C. M., Zhou, Y., Liu, F., & Licari, P. J. Isolation and characterization of new epothilone analogues from recombinant *Myxococcus xanthus* fermentations. *J. Nat. Prod.* 66, 1313-1317 (2003).

[14] Magarvey, N. A. et al. Biosynthetic characterization and chemoenzymatic assembly of the cryptophycins: potent anticancer agents from *Nostoc* cyanobionts. *ACS Chem. Bio,* 1, 766-779 (2006).

[15] Chai, Y. et al. Discovery of 23 Natural Tubulysins from *Angiococcus disciformisAn* d48 and *Cystobacter* SBCb004. *Chem. Biol.* 17, 296-309 (2010).

[16] Johnson, T. A. et al. Natural Product Libraries to Accelerate the High-Throughput Discovery of Therapeutic Leads. *J. Nat. Prod.* 74, 2545-2555 (2011).

[17] Butler. M. S. The Role of Natural Product Chemistry in Drug Discovery. *J. Nat. Prod.,* 67, 2141-2153 (2004).

[18] Singh, S. B., Young, K., & Miesel, L. Screening Strategies for Discovery of Antibacterial Natural Products. *Exp. Rev. Anti-Infect. Ther.* 9, 589-613 (2011).

[19] Cane, D. E., Walsh, C. T. & Khosla, C. Harnessing the biosynthetic code: combinations, permutations, and mutations. *Science* 282, 63-68 (1998).

[20] Nett, M., Ikeda, H. & Moore, B. S. Genomic basis for natural product biosynthetic diversity in the actinomycetes. *Nat. Prod. Rep.* 26, 1362-1384 (2009).

[21] Zazopoulos, E. et al. A genomics-guided approach for discovering and expressing cryptic metabolic pathways. *Nat. Biotechnol.* 21, 187-190 (2003).

[22] Johnston, C., Ibrahim, A. & Magarvey, N. Informatic strategies for the discovery of polyketides and nonribosomal peptides. *Medchemcomm* 3, 932-937 (2012).

[23] Challis, G. L. Genome Mining for Novel Natural Product Discovery. *J. Med. Chem.* 51, 2618-2628 (2008).

[24] Walsh, C. T., & Fischbach, M. A. Natural Products Version 2.0: Connecting Genes to Molecules. *J. Am. Chem. Soc.* 132, 2469-2493 (2010).

[25] Little, J. L., Williams, A. J., Pshenichnov, A., & Tkachenko, V. Identification of "Known Unknowns" Utilizing Accurate Mass Data and ChemSpider. *J. Am. Soc. Mass Spectrom.* 23, 179-185 (2012).

[26] Gutlein, M., Karwath, A. & Kramer, S. CheS-Mapper—Chemical Space Mapping and Visualization in 3D. *J. Cheminform.* 4, 7 (2012).

[27] Harrison, S. J., et al. A focus on the preclinical development and clinical statuse of the histone deacetylase inhibitor, romidepsin (depsipeptide, Istodax). *Epigen.* 5, 571-589 (2012).

[28] Mogi, T., Kita, K., Gramicidin S and polymyxins: the revival of cationic cyclic peptide antibiotics. *Cell. Mol, Life. Sci.* 66, 3821-3826 (2009).

[29] Van Bambeke, F. Glycopeptides and glycodepsipeptides in clinical development a comparative review of their antibacterial spectrum, pharmacokinetics and clinical efficacy. *Curr. Opin. Investig. Drugs.* 8, 740-749 (2006).

[30] Steenbergen, J. N., Alder, J., Thorne, G. M., Tally, F. P., Daptomycin: a lipopeptide antibiotic for the treatment of serious Gram-positive infections. *J. Antibmicrob. Chemother.* 55, 283-288 (2005).

[31] Newman D. J. Cragg, G. M., Meeting the Supply Needs of Marine Natural Products. *Handbook of Marine Natural Products* 26, 1295-1296 (2012).

[32] Eggen, M., Georg, G. I., The cryptophycins: their synthesis and anticancer activity. *Med. Res. Rev.* 22, 85-101 (2002)

[33] Weininger D, (1988) SMILES, a chemical language and information system. 1. Introduction to methodology and encoding rules. J Chem Inf Comut Sci 28:31-36.

[34] Chamrad D C, et al. (2004) Evaluation of algorithms for protein identification from sequence databases using mass spectrometry data. Proteomics 4:619-628.

[35] Eng J, McCormiack A L, Yates J R (1994) An approach to correlate tandem mass spectral data of peptides with amino acid sequences in a protein Database. J Am Soc Mass Spectrom 5:976-989.

[36] Zhang J, et al. (2011) PEAKS DB: De Novo sequencing assisted database search for sensitive and accurate peptide identification. Mol. Cell proteomics 11(4):M111.010587.

[37] Schwarzer D, Finking R, Marahiel M A (2003) Nonribosomal peptides: from genes to products. Nat Prod Rep 20:275-287.

[38] Fischbach M. Walsh C T (2006) Assembly-line enzymology for polyketide and nonribosomal peptide antibiotics: logic, machinery and mechanisms. Chem Rev 106:3468-3496.

[39] Caboche S, Pupin M, Leclere V, Fontaine A, Jacques P, Kucherov G (2008) NORINE: database of nonribosomal peptides. Nucl Acids Res 36:326-331.

[40] Paizes B, Suhai S (2004) Fragmentation pathways of protonated peptides. Mass Spectrometry Reviews 24:508-548.

[41] Razumovskaya J, et al. (2004) A computational method for assessing peptide-identification reliability in tandem mass spectrometry analysis with SEQUEST. Proteomics 4:961-969.

[42] Govaerts C, at al. (2002) Mass spectrometric fragmentation of cyclic peptides belonging to the polymyxin and colistin antibiotics studied by ion trap and quadrupole/orthogonal-acceleration time-of-flight technology. Rapid Commun Mass Spectrom 16(9):823-33.

[43] Vaisar T, Urban J (1998) Gas-phase Fragmentation of protonated mono-n-methylated peptides. Analogy with solution-phase acid-catalyzed hyrdolysis. J Mass Spectrom 33:505-525.

[44] Broerg A, Menkis A, Vasiliauskas R (2006) Kutznerides 1-4, Depsipeptides from the actinomycete *Kutzneria* sp. 744 inhabiting mycorrhizal roots of *Picea abies* seedlings. J Nat Prod 69:97-102.

45 Pohanka A, Menkis A, Levenfors J, Brober A (2006) Low-abundance kutznerides from *Kutzneria* sp. 744. J Nat Prod 69:1776-1781.

46 Barber M, et al. (1992) An investigation of the tyrothricin complex by tandem mass spectrometry. Int J Mass Spectrom Ion Processes 122:143-151.

47 Tang X, Thibault P, Boyd R (1992) Characterisation of the tyrocidine and gramicidin fraction of the tyrothricin complex from *Bacillus brevis* using liquid chromatography and mass spectrometry. Int J Mass Spectrom Ion Processes 122:153-179.

48 Pinel, N., Davidson, S. K. & Stahl, D. A. Verminephrobacter eiseniae gen. nov., sp. nov., a nephridial symbiont of the earthworm *Eisenia foetida* (Savigny). *Int. J. Syst. Eval. Microbial.* 58, 2147-2157 (2008).

49 Rausch, C., Weber, T., Kohlbacher, O., Wohlleben, W. & Huson, D. H. Specificity prediction of adenylation domains in nonribosomal peptide synthetases (NRPS) using transductive support vector machines (TSVMs). *Nuc. Acid. Res.* 33, 5799-5808 (2005).

50 Ansari, M. Z., Yadav, G., Gokhale, R. S. & Mohanty, D. NRPS-PKS: a knowledge-based resource for analysis of NRPS/PKS megasynthases. *Nuc. Acid. Res.* 32, W405-W413 (2004).

51 Stachelhaus, T., Mootz, H. D. & Marahiel, M. A. The specificity-conferring code of adenylation domains in nonribosomal peptide synthetases. *Chem. Biol.* 6, 493-505 (1999).

52 Darling, A. E., Mau, B. & Perna, N. T. progressiveMauve: multiple genome alignment with gene gain, loss and rearrangement. *PLoS One* 5, e11147 (2010).

53 Stachelhaus, T., Mootz, H. D. & Marahiel, M. A. The specificity-conferring code of adenylation domains in nonribosomal peptide synthetases. *Chem. Biol.* 6, 493-505 (1999).

54 Gamble, W. R. et al. Cytotoxic and tubulin-interactive hemiasterlins from *Auletta* sp. and *Siphonochalina* spp. sponges. *Bioorg. Med. Chem.* 7, 1611-1615 (1999).

55 Gutlein, M., Karwath, A. & Kramer, S. CheS-Mapper—Chemical Space Mapping and Visualization in 3D. *J. Cheminform.* 4, 7 (2012).

56 Schüller, A., Hahnke, V. & Schneider, G. SmiLib v2.0: A Java-Based Tool for Rapid Combinatorial Library Enumeration. *QSAR Combin. Sci.* 26, 407-410 (2007).

57 Banik, J. J. & Brady, S. F. Cloning and characterization of new glycopeptide gene clusters found in an environmental DNA megalibrary. *Proc. Natl. Acad. Sci. USA* 105, 17273-17277 (2008).

58 Seyedsayamdost, M. R. et al. Mixing and matching siderophore clusters: structure and biosynthesis of serratiochelins from *Serratia* sp. V4. *J. Am. Chem. Soc.* 134, 13550-13553 (2012).

59 Piel, J. et al. Antitumor polyketide biosynthesis by an uncultivated bacterial symbiont of the marine sponge *Theonella swinhoei*. *Proc. Natl. Acad. Sci. USA* 101, 16222-16227 (2004).

The invention claimed is:

1. A method of identifying one or more small molecule compounds from a mixture, the method comprising:
providing a mass spectrum of the mixture; and then
operating a computer processor in electronic communication with a computer-readable library to compare the mass spectrum of the mixture with calculated structures and corresponding calculated mass spectral fragmentation patterns of hypothetical small molecule compounds stored and electronically accessible in the computer-readable library,
wherein a mass spectral fragmentation pattern present in the mass spectrum of the mixture matching a calculated fragmentation pattern of one of the hypothetical compounds confirms the identity of a compound in the mixture as the hypothetical compound, and
wherein the small molecule compound is a chemical compound having a molecular weight of less than or equal to about 4000 Da.

2. The method of claim 1, wherein the small molecule compound has a fragmentation pattern that is predictable and/or discernible using computational methods that generate computer code representing hypothetical spectral fragments (hSFs) of chemical compounds by analyzing the structure of the chemical compound and assessing how an ionized form of the chemical compound will fragment or be generated from fragmentation induced within a mass spectrometer.

3. The method as defined in claim 1 wherein the computer-readable library further stores calculated mass spectral fragmentation patterns for known small molecule compounds; and, the method further comprises operating the computer processor in electronic communication with the computer-readable library to compare the mass spectrum of the mixture with calculated structures and corresponding calculated mass spectral fragmentation patterns for known small molecule compounds stored and electronically accessible in the computer-readable library, wherein
a mass spectral fragmentation pattern present in the mass spectrum of the mixture matching the calculated fragmentation pattern of one of the known compounds confirms the identity of a compound in the mixture as the known compound; and
the known small molecule compound is a chemical compound having a molecular weight of less than or equal to about 4000 Da.

4. The method of claim 3, wherein the structure and corresponding calculated fragmentation patterns of the known and hypothetical compounds are entered into the computer-readable library as input computer code for representing chemical compounds and the computer processor analyzes the code to identify known cleavage sites in the compounds to generate the hypothetical spectral fragments.

5. The method of claim 4, wherein the input computer code is SMILES code.

6. The method of claim 4, wherein the computer-readable library comprises computer code for structures and corresponding fragmentation patterns for analogs of the known and/or hypothetical small molecule compounds.

7. The method of claim 6, wherein the analogs of the known and/or hypothetical small molecule compounds are analogs resulting from in vivo post-translational modifications and/or post-isolation treatment methods that cleave of known groups.

8. The method of claim 7, wherein post-translational modifications are selected from one or more of glycosylations, hydroxylations, phosphoylations, sulfurations, formylations, acetylations, methylations, malonations, increases and decreases in chain length, oxidations and reductions.

9. The method of claim 7, wherein the post-isolation treatments are chemical and/or enzymatic treatments that are used to cleave the structure of the compounds.

10. The method of claim 7, wherein the post-isolation treatments are selected from one or more of deglycosylations, deacetylations, and dephosphylations.

11. The method of 6, wherein the analogs are predictable alternate forms of the known and/or hypothetical small molecule compounds.

12. The method of claim 11, wherein the predictable alternate forms are predicted based on known metabolic pathways, available metabolites and metabolite building blocks, genomes from other species that are known to produce similar compounds and/or genome sequencing of a species being analyzed.

13. The method of claim 3, wherein the one or more small molecule compounds and the known or hypothetical compounds belong to the same chemical class.

14. The method of claim 13, wherein the small molecule compound has a molecular weight of less than or equal to 3500, 3000, 2500, 2000 or 1000 Da.

15. The method of claim 3, wherein the method further comprises operating the computer processor to further assess the significance of the matching of the calculated fragmentation pattern of one of the known or hypothetical compounds with a mass spectral fragmentation pattern present in the mass spectrum of the mixture to confirm the identity of a compound in the mixture as the known or hypothetical compound.

16. The method of claim 15, wherein the significance of the match is scored mathematically.

17. The method of claim 3, wherein the one or more small molecule compounds comprise known compounds and the method is used to de-replicate the known compounds.

18. The method of claim 3, further comprising operating the computer processor to:
compare a genome of a microorganism with a genome of a microorganism known to produce one or more known small molecule compounds;
identify genes in the genome of the microorganism that are homologous to genes in the microorganism that produces the one or more known small molecule compounds;
if homologous genes are present in the microorganism, add calculated structures and corresponding calculated mass spectral fragmentation patterns for the one or more known small molecule compounds to the library; and
obtain a mass spectrum of an extract from the microorganism,
wherein a mass spectral fragmentation pattern present in the mass spectrum of the extract matching a calculated fragmentation pattern of one of the one or more known small molecule compounds confirms the identity of a compound in the extract as the known small molecule compound.

19. A system comprising a mass spectrometer, a computer processor and, optionally, a chromatographic separator wherein the computer processor is in communication with the mass spectrometer and chromatographic separator, if present, and comprises non-transitory computer readable medium, the computer readable medium comprising a series of instructions that, when executed by the processor, will perform the method according to claim 3, wherein the series of instructions cause the processor to perform one or more of the following:
(1) converting known and/or hypothetical small molecule compounds into computer readable code and calculating corresponding mass spectral fragmentation patterns of these small molecule compounds;
(2) creating a library of that comprises a calculated mass spectral fragmentation patterns for each known and/or hypothetical small molecule compound;
(3) comparing actual mass spectral fragmentation patterns of a mixture with the library comprising calculated mass spectral fragmentation patterns of known and/or hypothetical small molecule compounds; and
(4) identifying mass spectral fragmentation patterns present in the mass spectrum of the mixture matching a calculated fragmentation pattern of one of the known or hypothetical compounds and confirming the identity of a compound in the mixture as the known or hypothetical compound.

20. The method of claim 1, wherein the small molecule compound is selected from a nonribosomal peptide, a ribosomal peptide, a polyketide, a carbohydrate and a nucleic acid.

21. The method of claim 20, wherein the small molecule compound is selected from a nonribosomal peptide, a ribosomal peptide and a polyketide.

22. The method of claim 21, wherein the small molecule compound is a nonribosomal peptide.

23. The method of claim 1, wherein the small molecule compound is a naturally occurring compound.

24. The method of claim 1, wherein the mixture is complex mixture comprising a plurality of compounds obtained from a natural source.

25. The method of claim 24, wherein the natural source has been pre-treated, to increase, the production of one or more small molecule compounds.

26. The method of claim 1, wherein the mixture comprises, or is suspected of comprising, one or more biologically active compounds, or compounds that are of interest for their therapeutic potential.

27. The method of claim 1, wherein the method is used to screen mixtures from uncharacterized microorganisms to determine if the microorganisms produce small molecule compounds that exhibit structural similarities to compounds in the library.

28. A non-transitory computer-readable medium storing one or more sequences of instructions which, when executed by one or more processors, causes the one or more processors to perform the method of claim 1.

29. The method of claim 1, wherein the calculated mass spectral fragmentation patterns are selected from partial and total mass spectral fragmentation patterns.

30. The method of claim 1, wherein the computer-readable library comprises computer codes for structures and corresponding fragmentation patterns for compounds identified based on genomic sequences from a microorganism.

* * * * *